(12) United States Patent
Yodfat et al.

(10) Patent No.: US 10,603,432 B2
(45) Date of Patent: Mar. 31, 2020

(54) METHOD AND SYSTEM FOR ADAPTIVE COMMUNICATION TRANSMISSION

(71) Applicant: Roche Diabetes Care, Inc., Indianapolis, IN (US)

(72) Inventors: Ofer Yodfat, Maccabim-Reut (IL); Avihoo P. Keret, Kfar Vradim (IL); Zohar Man, Haifa (IL); Tsabar Mor, Naharia (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 168 days.

(21) Appl. No.: 15/431,908

(22) Filed: Feb. 14, 2017

(65) Prior Publication Data

US 2017/0151387 A1  Jun. 1, 2017

Related U.S. Application Data

(63) Continuation of application No. 13/124,194, filed as application No. PCT/IL2009/000981 on Oct. 18, 2009, now Pat. No. 9,566,383.

(Continued)

(51) Int. Cl.
  *A61M 5/172* (2006.01)
  *A61B 5/15* (2006.01)
  (Continued)

(52) U.S. Cl.
  CPC ....... *A61M 5/1723* (2013.01); *A61B 5/15087* (2013.01); *A61B 5/150862* (2013.01);
  (Continued)

(58) Field of Classification Search
  CPC .. A61M 2205/3525; A61M 2205/3592; A61M 2205/3569; A61M 2205/3561;
  (Continued)

(56) References Cited

U.S. PATENT DOCUMENTS

| 3,631,847 | A | 1/1972 | Hobbs |
| 3,771,694 | A | 11/1973 | Kaminski |

(Continued)

FOREIGN PATENT DOCUMENTS

| WO | 2007104755 A1 | 9/2007 |
| WO | 2008139458 A2 | 11/2008 |

(Continued)

OTHER PUBLICATIONS

International Search Report and Written Opinion dated Apr. 3, 2010 for PCT/IL2009/000921 Filed Oct. 18, 2009. pp. 1-7.

(Continued)

*Primary Examiner* — Nathan R Price
*Assistant Examiner* — Anh Bui
(74) *Attorney, Agent, or Firm* — Dinsmore & Shohl, LLP

(57) ABSTRACT

Disclosed are methods, systems, devices and articles, including a method for adaptive wireless communication transmissions between units of an ambulatory portable medical device. The method includes obtaining data relating to wireless transmissions between the units of the medical device, and setting one or more attributes of wireless transmission of one or more messages between the units of the medical device based, at least in part, on the obtained data.

16 Claims, 13 Drawing Sheets

Related U.S. Application Data

(60) Provisional application No. 61/106,041, filed on Oct. 16, 2008.

(51) Int. Cl.
*H04W 52/22* (2009.01)
*H04W 52/20* (2009.01)
*G16H 40/40* (2018.01)
*G06F 19/00* (2018.01)
*H04W 12/00* (2009.01)
*A61M 5/142* (2006.01)
*H04W 52/24* (2009.01)
*H04W 12/04* (2009.01)

(52) U.S. Cl.
CPC ... *A61B 5/150877* (2013.01); *A61M 5/14228* (2013.01); *A61M 5/14248* (2013.01); *G06F 19/3468* (2013.01); *G16H 40/40* (2018.01); *H04W 12/003* (2019.01); *H04W 52/20* (2013.01); *H04W 52/22* (2013.01); *H04W 52/221* (2013.01); *H04W 52/226* (2013.01); *H04W 52/228* (2013.01); *H04W 52/243* (2013.01); *H04W 52/248* (2013.01); *A61B 2560/045* (2013.01); *A61M 2005/14268* (2013.01); *A61M 2205/3306* (2013.01); *A61M 2205/3569* (2013.01); *A61M 2205/3592* (2013.01); *A61M 2230/201* (2013.01); *H04W 12/04* (2013.01)

(58) Field of Classification Search
CPC . A61M 2205/3507; A61M 2205/3523; H04W 24/00; H04W 52/12; H04W 52/20; H04W 52/24; H04W 52/46; H04W 52/22; H04W 52/221; H04W 52/226; H04W 52/228; A61B 5/0002; A61B 5/150862; A61B 5/15087; A61B 5/150877; A61B 2560/045; H04B 7/18543; H04B 17/003; H04L 43/50; H04L 43/0852; H04L 43/08; H04L 1/0003; H04L 1/0026
See application file for complete search history.

(56) References Cited

U.S. PATENT DOCUMENTS

| | | |
|---|---|---|
| 4,494,950 A | 1/1985 | Fischell |
| 4,544,369 A | 10/1985 | Skakoon et al. |
| 4,657,486 A | 4/1987 | Stempfle et al. |
| 5,558,640 A | 9/1996 | Pfeiler et al. |
| 5,957,895 A | 9/1999 | Sage et al. |
| 6,263,246 B1 | 7/2001 | Goedeke et al. |
| 6,485,461 B1 | 11/2002 | Mason et al. |
| 6,589,229 B1 | 7/2003 | Connelly et al. |
| 6,723,072 B2 | 4/2004 | Flaherty et al. |
| 6,740,059 B2 | 5/2004 | Flaherty |
| 2003/0114897 A1 | 6/2003 | Von Arx et al. |
| 2007/0106218 A1 | 5/2007 | Yodfat et al. |
| 2007/0191702 A1 | 8/2007 | Yodfat et al. |
| 2008/0214916 A1 | 9/2008 | Yodfat et al. |
| 2008/0215035 A1 | 9/2008 | Yodfat et al. |
| 2009/0149803 A1 | 6/2009 | Estes et al. |
| 2010/0069890 A1 | 3/2010 | Graskov et al. |
| 2010/0167385 A1 | 7/2010 | Celentano et al. |
| 2010/0168660 A1 | 7/2010 | Galley et al. |
| 2010/0241086 A1 | 9/2010 | Yodfat et al. |
| 2011/0176490 A1* | 7/2011 | Mehta .................. A61B 5/0002 370/328 |

FOREIGN PATENT DOCUMENTS

| | | |
|---|---|---|
| WO | 2009001337 A2 | 12/2008 |
| WO | 2009013736 A1 | 1/2009 |
| WO | 2009066287 A2 | 5/2009 |
| WO | 2009066288 A1 | 5/2009 |
| WO | 2009125398 A2 | 10/2009 |

OTHER PUBLICATIONS

W. Schubert et al., "An implantable artificial pancreas," Medical and Biological Engineering & Computing, 1980, 18, pp. 527-537.

\* cited by examiner

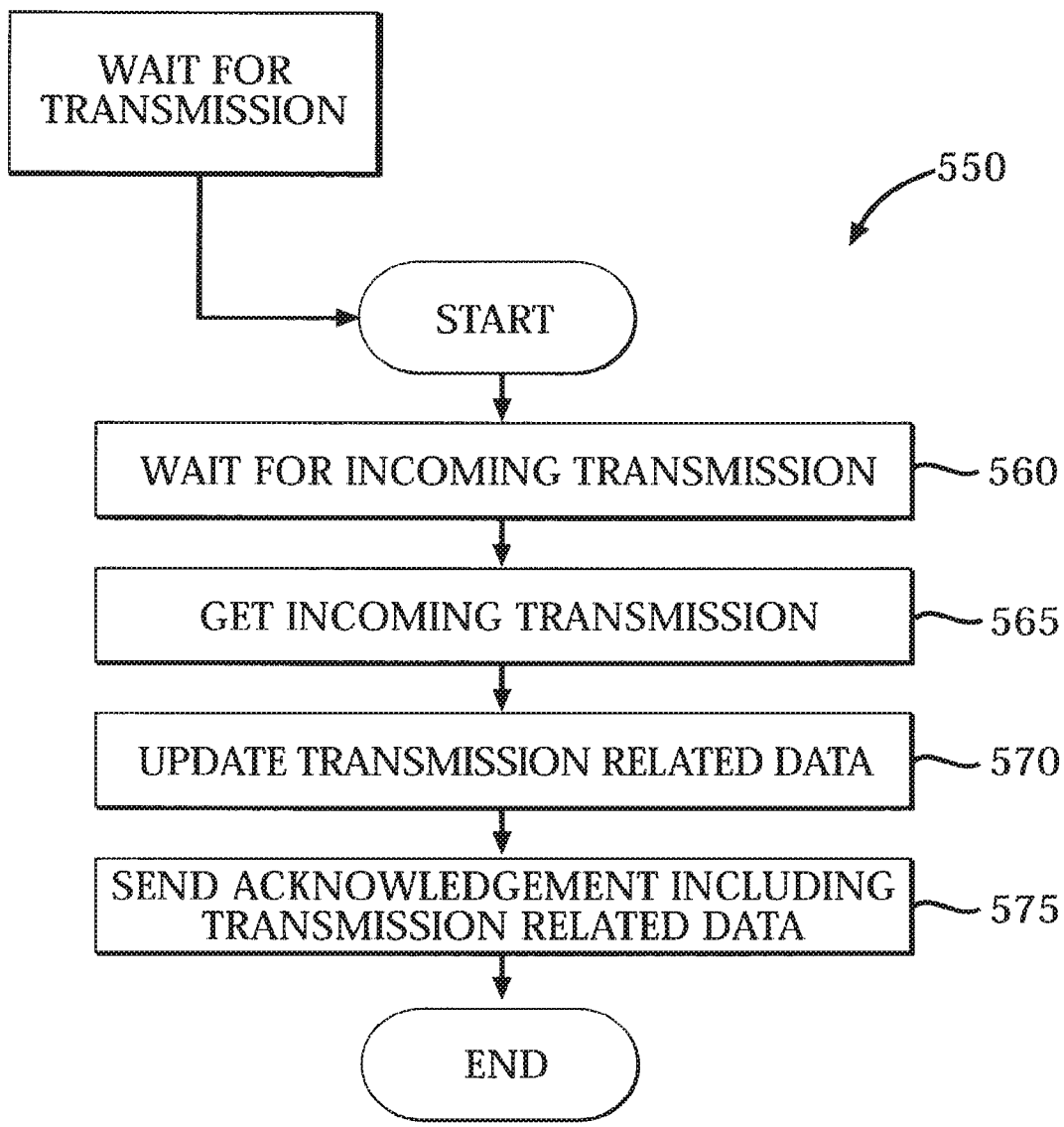

METHOD AND SYSTEM FOR ADAPTIVE COMMUNICATION TRANSMISSION

CROSS-REFERENCE TO RELATED APPLICATIONS

This application is a continuation of U.S. application Ser. No. 13/124,194, filed Jun. 28, 2011, which is a U.S. national stage entry of International Application No. PCT/IL2009/000981, filed Oct. 18, 2009, and which claims priority to provisional U.S. application Ser. No. 61/106,041, entitled "Method and System for Adaptive Communication Transmission" filed Oct. 16, 2008, the content of which is hereby incorporated by reference in its entirety.

FIELD OF THE DISCLOSURE

The present disclosure relates generally to robust, power saving and adjustable communication systems, and to systems, devices and methods to be used by a medical dispensing device/system. In particular, the present disclosure relates to portable infusion devices/systems for delivery of therapeutic fluids (e.g., insulin) that can be attached to a body of a patient and that include a reusable part and a disposable part.

BACKGROUND OF THE DISCLOSURE

Portable Dispensing Devices

Medical treatment of some illnesses requires continuous (or periodic) drug infusion into various body compartments through, for example, subcutaneous and intra-venous injections. Diabetes mellitus patients, for example, require administration of varying amounts of insulin throughout the day to control the blood glucose levels. In recent years, ambulatory portable insulin infusion pumps have emerged as superior alternatives to multiple daily syringe injections of insulin. These pumps, which deliver insulin at a continuous, or periodic, basal rate as well as in bolus volumes, were developed to liberate patients from repeated self-administered injections, and to allow them to maintain a near-normal daily routine. Both basal and bolus volumes generally have to be delivered in precise doses, according to an individual prescription, since an overdose or under-dose of insulin could be fatal.

The first generation of portable insulin pump included "pager-like" devices attached to patients' belts. A first generation device included a reservoir within the device housing. A long tube delivered insulin from the pump attached to a patient's belt to a remote insertion site. Examples of such first generation devices are described, for example, in U.S. Pat. Nos. 3,631,847, 3,771,694, 4,657,486 and 4,544,369, the contents of all of which are hereby incorporated by reference in their entireties. These first generation devices included a control panel combined with the pump, resulting in a device with relatively large dimensions. Although bulky, large, and heavy, these first generation devices were an improvement over multiple daily injections. Nevertheless, the first generation devices were uncomfortable, bulky devices with long tubes. Consequently, these first generation devices were rejected by the majority of diabetic insulin users because the devices impacted regular activities, such as sports (e.g., swimming).

To avoid the noted consequences of using a long delivery tube of the infusion set, a new concept, referred to as a second generation pump, was proposed. This concept included a remote controlled skin securable (e.g., adherable) device with a housing having a bottom surface adapted to be secured to the patient's skin, a reservoir disposed within the housing, and an injection needle in fluid communication with the reservoir. These skin securable devices were generally discarded every 2-3 days, in a manner similar to that existing with other commercial pump infusion sets. Second generation devices are disclosed, for example, in U.S. Pat. No. 5,957,895 to Sage, U.S. Pat. No. 6,589,229 to Connelly and U.S. Pat. No. 6,740,059 to Flaherty, the contents of all of which are hereby incorporated by reference in their entireties. Additional configurations of skin securable pumps are disclosed, for example, in U.S. Pat. No. 6,723,072 to Flaherty and U.S. Pat. No. 6,485,461 to Mason, the contents of all of which are hereby incorporated by reference in their entireties.

The second generation skin securable infusion devices are typically heavy and bulky and generally cause discomfort when carried by the user. Additionally, these devices are relatively expensive. The entire device, including the relatively expensive components (e.g., electronic modules, a driving mechanism, etc.) is generally discarded every 3 days or so. Furthermore, although there are situations in which patients would like to temporarily disconnect the pump (e.g., when taking hot showers, entering a sauna, etc.), these second-generation devices cannot be reconnected after being disconnected.

Third generation devices provides a more cost-effective solution and allow more diverse use of an infusion device. An improvement to this third generation skin securable pumps includes the use of two parts, as described, for example, in co-pending/co-owned U.S. patent application Ser. No. 12/004,837 and International Patent Application No. PCT/IL07/001578, the contents of which are hereby incorporated by reference in their entireties. These applications disclose embodiments directed to systems, devices and methods for connecting and disconnecting a skin securable dispensing unit/device. Such embodiments sometimes utilize a cradle unit which is initially adhered to the skin and then has a cannula inserted through the cradle unit into the body of the user. Insertion can be performed automatically by a dedicated inserter device, or may be performed manually. The dispensing unit of the device can also be connected and disconnected to and from the skin-adhered cradle at the patient's discretion. This implementation enables versatile operational modes, including manual and automatic cannula insertion modes, use of cannulae with various lengths and insertion of a cannula at various insertion angles. The cradle is disposable and relatively inexpensive and may be discarded every 2-3 days. Unlike second generation infusion pumps, in situations involving site misplacement of the cannula (resulting in scarred tissue, bleeding, cannula kinking etc.), only the cradle and cannula may have to be disposed and replaced, rather than the whole (and relatively expensive) device which includes the reservoir still containing unused insulin.

Ambulatory portable drug delivery devices and some medical sensors require a relatively large volume of information relating to parameters and conditions of the treatment, the device and medical/health state of the patient. Such information and data typically include characteristics of the drug dosage, data relating to the conditions of the patient's body and data associated with the device operation. The data is typically transferred between a remote control, dispensing device and sensors for measuring bodily level analyte (e.g., glucose), via, for example, wireless RF communication.

Dispensing Device and Remote Control Communication

Transmitting the data between a dispensing device and a remote control (also referred to as a remote control unit and/or remote controller, together with the dispensing device may also be referred to as a dispensing system; each also may be individually referred to as a unit, where a device may comprise one or more units) give rise to certain problems. First, the transmission between a remote control and a dispensing device may be corrupted or disrupted, e.g., the signal may be corrupted due to low signal to noise ratio (SNR). Another drawback is that there are only a limited number of frequencies open for transmissions, e.g., the frequencies in the Industrial, Scientific, and Medical (ISM) radio band. However, the ISM radio band may be supporting many other wireless devices, such as wireless devices equipped with WiFi, Bluetooth, wireless USB and the like. These wireless transmission techniques and protocols are used by many devices, such as cordless telephones, cellular phones and their accessories, personal computers, hand held computers, and the like. Furthermore, there are additional devices, such as microwave ovens, switches, and electric motors that cause radio frequency interference (RFI) in the ISM radio band. As wireless and miniaturization technologies improve, electrical devices' reliance on wireless as a mechanism for communications will continue to rise, thus exacerbating interference problems (e.g., causing jamming and noise problems). The multiplicity of communications and messages sharing similar (or the same) frequencies may also give rise to problems related to receiving false messages, jamming, low signal to noise ratio, high radio frequency interference and the like.

Communications problems and programming of infusion pumps may be particularly critical with respect to implantable devices. Implantable infusion pumps for infusion of, e.g., insulin, are described, for example, in U.S. Pat. Nos. 4,494,950 and 5,558,640 and in the publication by W. Schubert et al., "An implantable artificial pancreas," Medical and Biological Engineering & Computing, 1980, 18, pp. 527-537, the contents of all of which are hereby incorporated by reference in their entireties. In the latter document, an artificial implantable pancreas is described in which in a first mode of operation, a glucose sensor transmits the actual blood glucose level to a control unit, and the amount of insulin to be infused may then be calculated on the basis of patient specific parameters recorded in a program memory. Corresponding control signals for a dosing unit to be infused may subsequently be determined by performing a control procedure. If no sensor is used or if the sensor employed fails, the dosing unit is controlled in accordance with a second mode of operation by a stored dosing program. Thus, the first mode of operation corresponds to a closed control loop and the second mode of operation corresponds to an open control loop.

Safe operation of a remotely controlled delivery device typically depends, at least in part, on control commands sent from a remote control unit. The commands should be received only by the specific delivery device that is to be controlled. Other delivery devices in the vicinity of the user that also happen to receive the transmitted command should not perform operations in response to such received commands. Further, as the delivery device may be adapted to transmit data to the remote control, such information should generally be received and acted upon only by the corresponding control unit. Such an implementation issue has to be considered with respect to both second and third generation dispensing devices. To provide proper security, any two units intended to work together will normally be "paired" by exchange of information between the two units, enabling robust data communication between the two units (e.g., employing some recognition and/or encoding procedure unique to that particular pair of devices).

A medical system that includes a safe pairing mechanism is described, for example, in International Patent Publication No. WO 2007/104755, the content of which is hereby incorporated by reference in its entirety. In that system, a medical system is provided comprising a first unit and a second unit. Both of the units includes two communication mechanisms, the first having a short range (e.g., Near Field Communication) for transmitting and receiving some of the communications, particularly pairing commands and commands related to bolus delivery, and a second communication mechanism having a longer range (and thus less secured) for communicating other massages. Including two communication mechanisms in the same unit may result in bigger and bulkier housing and in higher costs.

SUMMARY

In view of the foregoing, in some embodiments, systems, devices and methods to enable secure pairing and communication of two electronically controlled units of, for example, a dispensing device, adapted to communicate with each other is provided. Communication may be either one-way or two-way. In some embodiments, systems, devices and methods which provide adaptive communication according to determined transmission medium properties (e.g., RFI, SNR, etc.) and according to the presence of other communication transmissions (e.g., transmission between another pair of dispensing devices) in the vicinity of the two devices that are to communicate.

Some remotely controlled ambulatory medical devices use the ISM radio frequencies. Such devices often communicate with one paired remote control, i.e., both of the units recognize each other's transmissions and ignore transmissions from other devices.

Recognition may be established using an identifier included in the transmission, the structure/format of the message (e.g., the communication protocol used), encryption key(s) used, use of matching keys, etc.

During performance of pairing procedures to match devices that include wirelessly communicating units, other devices may interfere, resulting in mismatched paired devices, e.g., a remote control of one user may be paired to a dispensing unit of another user. This risk of communication mismatch increases in environments in which multiple devices communicate in close proximity of each other (e.g., in crowded areas, such as malls, theaters, etc.).

Communication problems, such as high RFI level, multiple devices that use the same frequencies and implement similar transmission techniques, may occur. These problems can be reduced by adjusting the transmission power, and/or filtering received transmissions based on the power/quality of the received transmission. Another approach to reduce the occurrence of communication problems is to provide at least one frequency for the use of paired units and at least one other frequency for the use of another paired unit.

To reduce communication problems resulting from, for example, high RFI level, miscommunication and processing of irrelevant transmission, the transmitting and/or receiving units of the device may agree upon the frequencies to use. Thus, fewer transmissions will share the same frequencies, resulting in decreased RFI level and other communication-related interferences.

Fluid delivery systems or devices may include at least two of:

- A remote control that may include, for example, a blood-glucose monitor (BGM);
- A dispensing/patch unit;
- A sensor to monitor glucose levels by optical, electro-chemical, chemical, reciprocating mechanisms; and
- An integrated dispensing and sensing unit.

Such delivery systems may also include such external devices, such as a PC, a laptop, a Personal Digital Assistant ("PDA"), a cellular phone, a media player (e.g., iPod), other types of processor-based devices, or any other type of remote commander/controller. (The term "delivery device" may refer to any of dispensing patch unit, ambulatory dispensing device for treating diabetes and/or diabetes related health condition, sensor for measuring health parameter related to diabetes and combinations of these devices, e.g., dispensing patch unit with glucose sensor module. These terms may be used interchangeably hereinafter).

Thus, procedures to adjust and/or determine attributes of communication transmissions to reduce communication problems and enable reliable communication in environments susceptible to high levels of interference are disclosed.

In some embodiments of the present disclosure, reliable communications between a remote control and an infusion pump secured to the patient are provided. An example of such a system (a third-generation system/device) that includes a remote control and an infusion pump is described, for example, in co-pending/co-owned U.S. patent application Ser. No. 11/397,115 and also in International Patent Applications Nos. PCT/IL06/001276 and PCT/IL09/000388, the contents of all of which are hereby incorporated by reference in their entireties. In a third generation device, a dispensing unit is employed that is composed of two parts: a reusable part that may include a driving mechanism, communication mechanism, electronic modules, and other relatively expensive components, and a disposable part containing relatively inexpensive components such as a reservoir, and a power source (which may be part of the reusable and/or the disposable part, or a separate component).

Reliable communications in such portable systems may be used to support continuous monitoring of glucose. The continuous monitoring device can be incorporated within the dispensing device, thus providing the device with both sensing and dispensing capabilities. An example of such a device is described, for example, in co-pending/co-owned U.S. patent application Ser. Nos. 11/989,665 and 11/963,481, the contents of which are hereby incorporated by reference in their entireties.

The present disclosure describes various embodiments of methods, apparatuses and systems, including (for example) computer program products, for adjustable wireless transmissions used with an external, miniature, portable, programmable fluid dispensing unit configured to communicate with a remote control having processing functionality.

In some embodiments, a small, low cost, portable dispensing unit that includes a disposable part and a reusable part is provided. The unit's processing functionality may be implemented in one or more parts of the system and/or by providing a telemetry module, e.g., a wireless communication mechanism to enable communication between the dispensing unit and the remote control.

In some embodiments, a method for wireless communication between a remote control unit and at least one of a dispensing unit for delivering medicinal fluids and/or a sensor for measuring glucose level is provided. The method may include changing a band for transmission to reduce the transmission power and/or the level of interferences to the transmission. The transmissions include data representative of at least one of, for example, patient information, a level of blood glucose, a status of the dispensing device and/or a therapeutic dosage. The power of transmission may be adjusted by changing the transmission range and/or reducing interferences in the communication band. In some embodiments, the wireless transmission is RF transmission. In some embodiments, the RF transmission uses the ISM bands.

In the present disclosure, the term unit(s) may sometimes be used interchangeably with the term device(s), and the term device(s) may sometimes be used interchangeably with the term system(s). Such uses include, for example, a device comprising one or more (and preferably two or more) units, and a system comprising one or more (and preferably two or more) devices. Moreover, a system may also comprise one or more units.

In some embodiments, a method for adaptive wireless communication transmissions between units of an ambulatory portable medical device is disclosed. The method includes obtaining data relating to wireless transmissions between the units of the medical device, and setting one or more attributes of wireless transmission of one or more messages between the units of the medical device based, at least in part, on the obtained data.

Embodiments of the method may include any of the following features.

The method may further include communicating the one or more messages between a first unit and a second unit of the medical device via wireless transmission configured with the one or more attributes.

Setting the one or more attributes of the wireless transmission of the one or more messages may include determining a power level of the wireless transmission of the one or more messages based on the obtained data.

The method may further include transmitting the one or more messages at the determined power level from one of the units of the medical device to another of the units of the medical device.

The method may further include, in response to receiving the one or more messages transmitted, sending an acknowledgement, by the other of the units of the medical device, to the one of the units of the medical device.

The method may further include increasing the determined power level based on a determination that an acknowledgement responsive to the transmitted one or more messages was not received.

Setting the one or more attributes of the wireless transmission of the one or more messages may include determining at least one frequency of the wireless transmission of the one or more messages based on the obtained data.

The method may further include transmitting the one or more messages at the at least one determined frequency from one of the units of the medical device to another of the units of the medical device.

The method may further include, in response to receiving the one or more messages transmitted, sending an acknowledgement, by the other of the units of the medical device, to the one of the units of the medical device.

The method may further include determining at least one other frequency upon a determination that an acknowledgement responsive to the transmitted one or more messages was not received.

Setting the one or more attributes of the wireless transmission of the one or more messages may include determining a power level and at least one frequency of the wireless transmission of the one or more messages based on the obtained data.

The method may further include transmitting the one or more messages at the at least one determined frequency and the determined power level from one of the units of the medical device to another of the units of the medical device.

The method may further include performing one of determining another frequency and increasing the power level upon a determination that an acknowledgement responsive to the transmitted one or more messages was not received.

The medical device may include a therapeutic fluid dispensing device, and setting one or more attributes of the wireless transmission of the one or messages may include setting one or more attributes of the wireless transmission between two or more of, for example, a remote control to control at least some of the operations of the dispensing device, a dispensing unit to deliver therapeutic fluid into a body of a patient and/or a sensor to monitor glucose levels in the body of the patient.

Obtaining data may include determining one or more transmission related values based on one or more of, for example, data transmitted from an external data source and/or measured data.

Determining one or more transmission related values may include computing at least one of one or more transmission related values using mathematical relations relating the at least one of the one or more values to at least one of the one or more of, for example, the data transmitted from the external data source and/or the measured data.

The one or more transmission related values may include one or more of, for example, availability of transmission frequencies, frequency hopping schedules, pairing status of at least some of the units of the medical device, radio-frequency interference (RFI) level in an area in which the units of the medical device are located, signal-to-noise ratio (SNR) of a first one or more previous transmissions communicated by the units of the medical device and/or Received Signal Strength Indication (RSSI) data of a second one or more previous transmissions.

The method may further include notifying a user regarding at least one of, for example, the data relating to wireless transmissions and/or the one or more attributes of the wireless transmissions.

The medical device may include one or more of, for example, a therapeutic fluid dispensing device and an analyte sensing device.

In some embodiments, a medical system is disclosed. The system includes at least two of, for example, a dispensing unit to dispense therapeutic fluid to a body of a patient, a sensor to monitor analyte concentration levels in the body of the patient and/or a remote control to control operations of the at least one of the dispensing unit and the sensor. A first unit from at least one of the dispensing unit, the remote control and/or the sensor is configured to obtain data relating to wireless transmission of one or more messages between the first unit and a second unit from the at least one of the dispensing unit, the remote control and/or the sensor, and set one or more attributes of the wireless transmission of the one or more messages between the first unit and the second unit based on the obtained data.

Embodiments of the system may include one or more of the above-described features of the method, as well as any of the following features.

The first unit may further be configured to communicate the one or more messages between the first unit and the second unit via wireless transmission configured with the one or more attributes.

The first unit configured to set the one or more attributes of the wireless transmission of the one or more messages may be configured to determine a power level of the wireless transmission of the one or more messages based on the obtained data.

The first unit may further be configured to transmit the one or more messages at the determined power level to the second unit.

The second unit may be configured to, in response to receiving the one or more messages transmitted by the first unit, send an acknowledgement to the first unit.

The first unit may further be configured to increase the determined power level based on a determination that an acknowledgement responsive to the transmitted one or more messages was not received from the second unit.

The first unit configured to set the one or more attributes of the wireless transmission of the one or more messages may be configured to determine at least one frequency of the wireless transmission of the one or more messages based on the obtained data.

The first unit may further be configured to transmit the one or more messages at the at least one determined frequency to the second unit.

The second unit may be configured to, in response to receiving the one or more messages transmitted from the first unit, send an acknowledgement to the first unit.

The first unit may further be configured to determine at least one other frequency upon a determination that an acknowledgement responsive to the transmitted one or more messages was not received.

The first unit configured to set the one or more attributes of the wireless transmission of the one or more messages may be configured to determine a power level and at least one frequency of the wireless transmission of the one or more messages based on the obtained data.

The first unit may further be configured to transmit the one or more messages at the at least one determined frequency and the determined power level to the second unit.

The first unit may further be configured to perform one of determining another frequency and increasing the power level upon a determination that an acknowledgement responsive to the transmitted one or more messages was not received.

The first unit configured to obtain data may be configured to determine one or more transmission related values based on one or more of, for example, data transmitted from an external data source and/or measured data.

The first unit configured to determine one or more transmission related values may be configured to compute at least one of one or more transmission related using mathematical relations relating at least one of the one or more values to at least one of the one or more of, for example, the data transmitted from the external data source and/or the measured data.

Details of one or more implementations are set forth in the accompanying drawings and in the description below. Further features, embodiments, aspects, and advantages will become apparent from the description, the drawings, and the claims.

BRIEF DESCRIPTION OF THE DRAWINGS

FIGS. 5a-b are flowcharts of processes for adjusting transmission power, at the transmitting part (FIG. 5a) and at the receiving part (FIG. 5b).

DETAILED DESCRIPTION OF THE DISCLOSURE

Disclosed are methods, systems and devices for adaptive wireless communication transmissions between units/modules of an ambulatory portable fluid dispensing device. In some embodiments, a method is disclosed that includes receiving data relating to wireless transmissions between the units of the fluid dispensing system, and setting one or more attributes of wireless transmission between the units of the fluid dispensing system of one or more messages based, at least in part, on the received data.

Figure 1A:
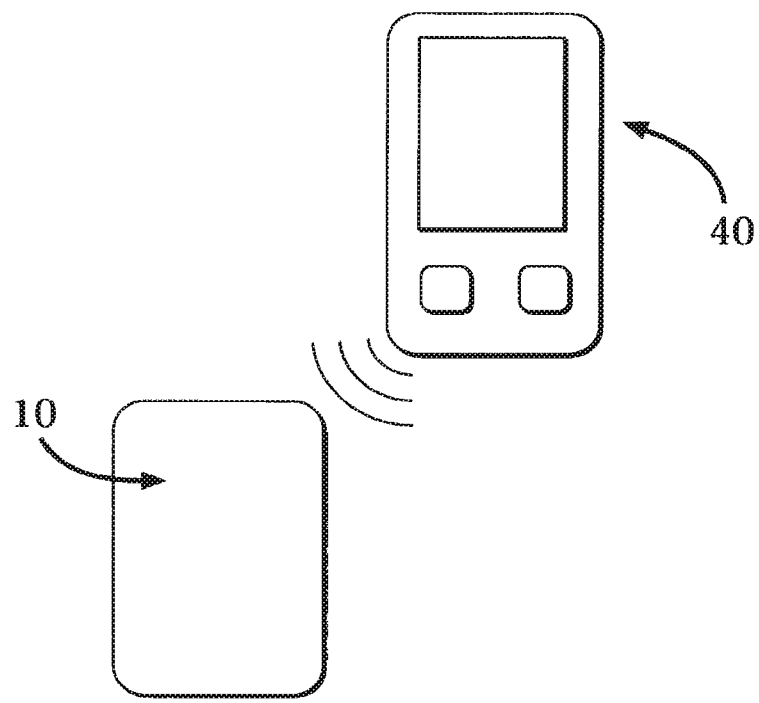
FIGS. 1a-b are schematic diagrams of a device having a dispensing unit and a remote control unit.
Figure 1B:
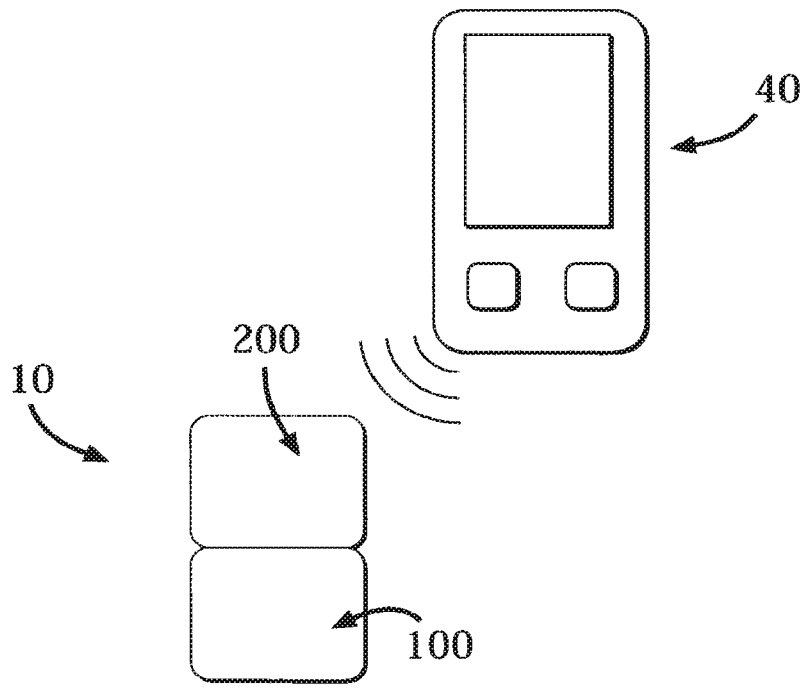

Referring to FIGS. 1a-b, schematic diagrams of an exemplary device having a dispensing unit 10 to dispense therapeutic fluid(s) (e.g., insulin) and/or sense analyte(s) (e.g., glucose) (the dispensing unit may also be referred to as a "patch" or "patch unit") and a remote control 40 (also referred to as a "remote control unit") are shown. In some embodiments, the dispensing unit 10 can include a single part (as shown FIG. 1a) or two parts (as shown FIG. 1b), e.g., a reusable part 100 and a disposable part 200.

In some embodiments, fluid delivery can be programmed by the remote control 40 and/or by manual buttons (not shown) constituting part of a user interface provided on the dispensing unit 10. Embodiments of such arrangements are disclosed, for example, in co-owned/co-pending International Patent Application No. PCT/IL08/001001, filed Jul. 20, 2008, claiming priority to U.S. Provisional Patent Application No. 60/961,527, filed Jul. 20, 2007, and entitled "Manually Operable Portable Infusion Device", the contents of all of which are hereby incorporated by reference in their entireties. Generally, each of the remote control 40 and the dispensing unit 10 includes a communication module (not shown), e.g., a transceiver, to enable wireless and/or wired communication.

Figure 2A:
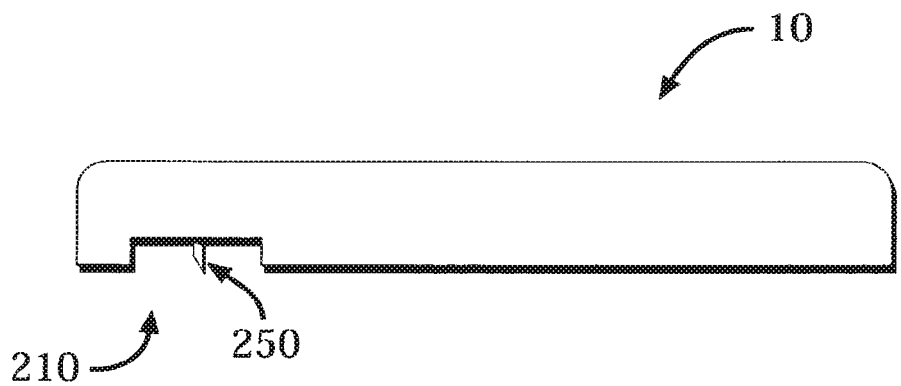
FIGS. 2a-c are schematic diagrams of a fluid delivery device that includes a dispensing unit that can be composed of one part (2a) or two-parts (2b), and can further include a cradle unit and a cannula cartridge unit (2c).
Figure 2B:
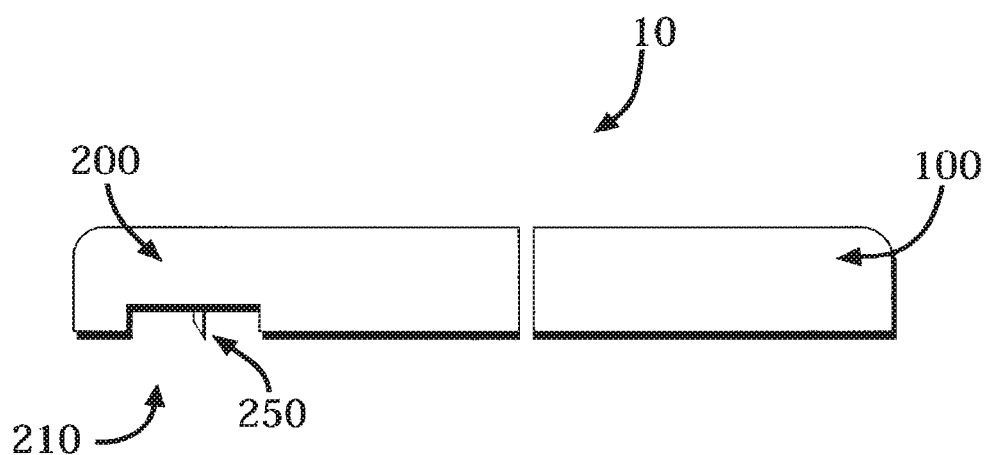
Figure 2C:
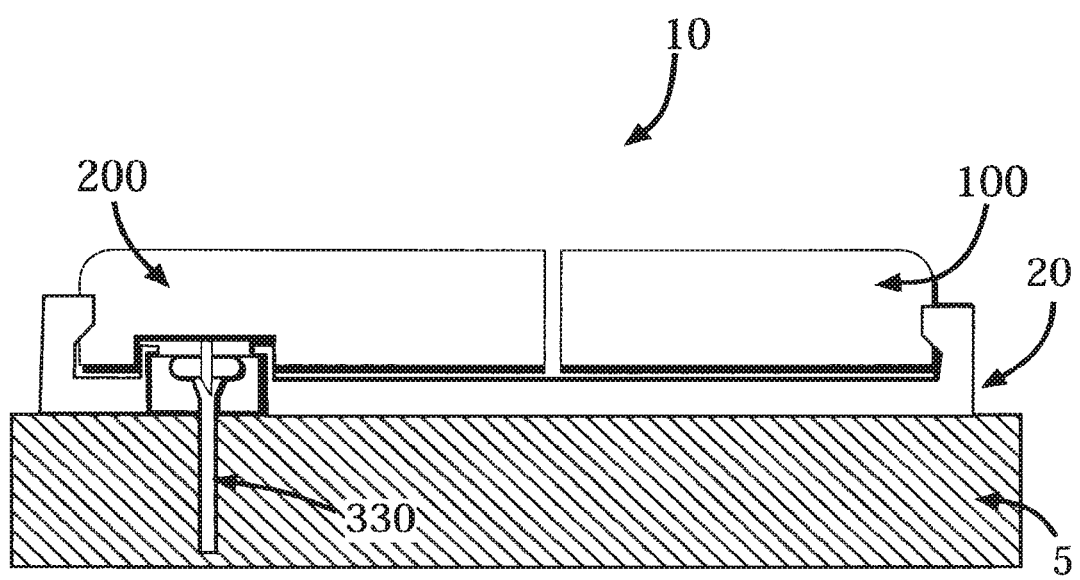

Referring to FIG. 2a, FIG. 2b and FIG. 2c, schematic diagrams of fluid dispensing device according to some embodiments that includes a dispensing unit 10 are shown. As depicted in FIGS. 2a-2b, the dispensing unit 10 of the fluid delivery device may include on its bottom surface (the surface that comes in contact with the patient) an outlet port 210 and a connecting conduit 250 capable of being in fluid communication with the patient's body. The conduit 250 may also be configured to enable fluid escape during priming. The dispensing unit 10 may include a single part (see, for example, FIG. 2a) or two parts (see, for example, FIG. 2b). The two-part dispensing unit 10 may be composed of a reusable part 100 and a disposable part 200. In the embodiment shown in FIG. 2b, the outlet port 210 and the connecting conduit 250 are located at the bottom surface of the disposable part 200. The fluid delivery device can further include a cradle 20 (also referred to as a cradle unit) and a cannula 330, as illustrated in FIG. 2c. The two-part dispensing unit 10 in some embodiments is connected to the cradle 20, which may be, for example, a skin adherable cradle (the skin is identified using reference numeral 5). Fluid communication between the dispensing unit 10 and the patient's body is enabled by virtue of the cannula 330 which is a subcutaneously insertable tube.

Figure 3A:
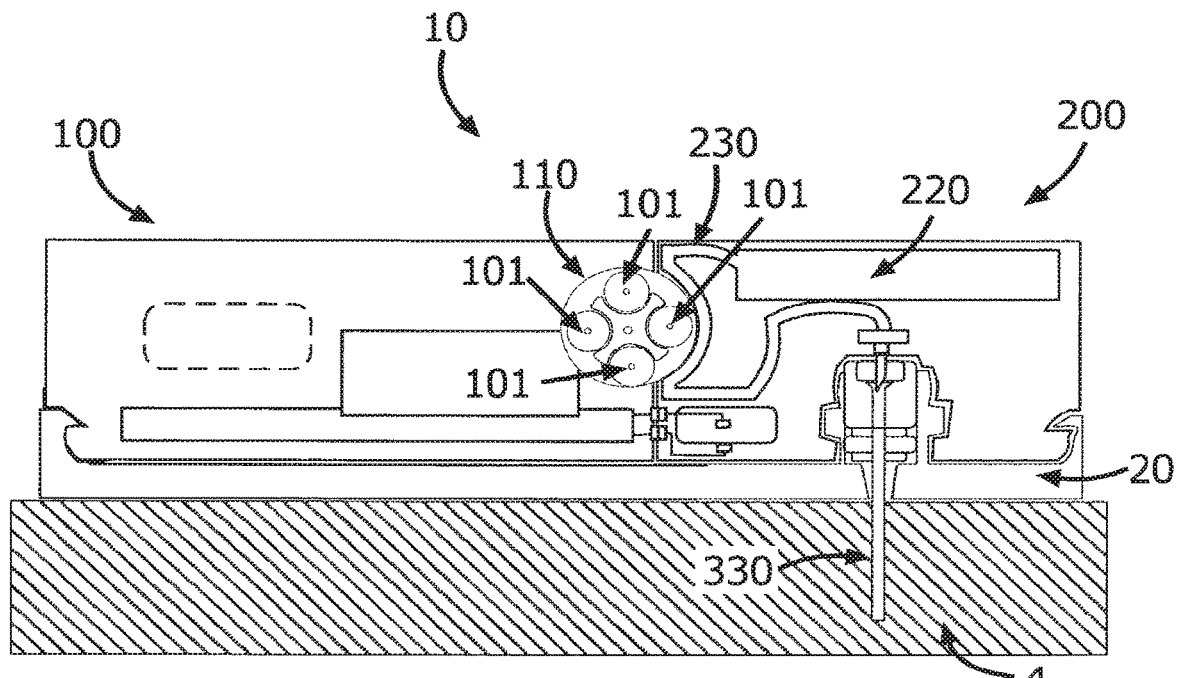
FIGS. 3a-d are schematic diagrams of dispensing (patch) units configured to be connectable to a skin adherable cradle.
Figure 3B:
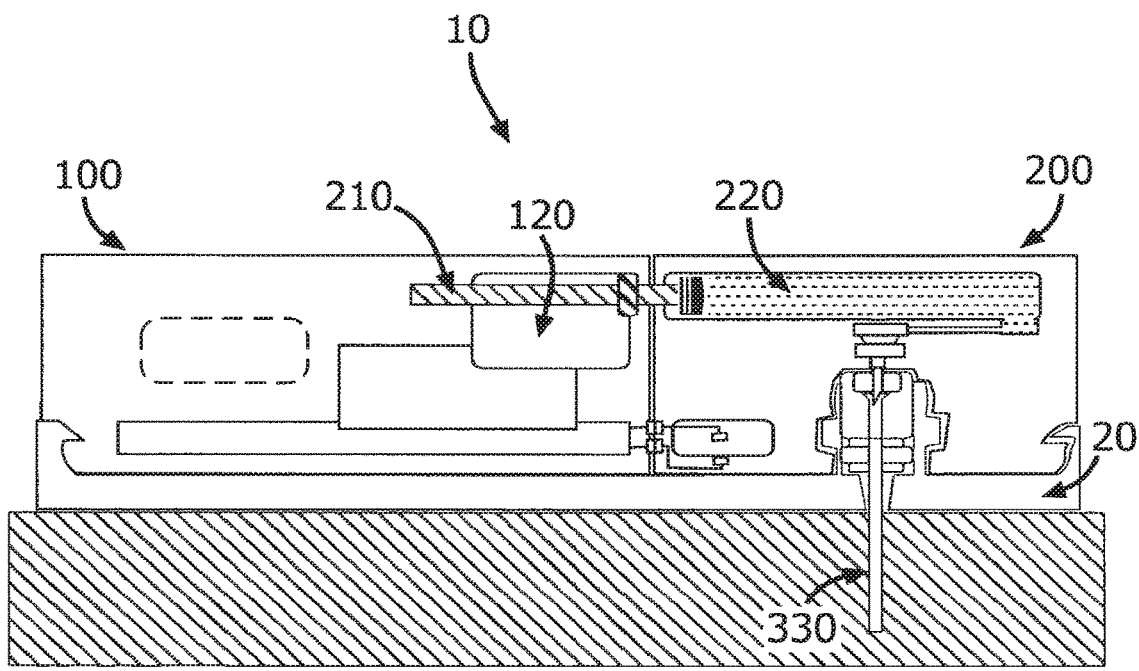

Referring to FIGS. 3a-d, schematic diagrams of dispensing units configured to be attached to a cradle 20 are shown. FIG. 3a illustrates a fluid delivery device that includes a cradle 20 and a two-part dispensing unit 10 that employs a peristaltic pumping mechanism. Rotation of a rotary wheel 110 and periodic pressing of rollers 101 against a delivery tube 230 positively displaces fluid from a reservoir 220 into the delivery tube 230 by virtue of a peristaltic motion. The fluid is then delivered via the cannula 330 into the subcutaneous compartment 4 within the patient's body. A two-part dispensing unit employing a peristaltic pumping mechanism is also described, for example, in co-pending, co-owned U.S. patent application Ser. No. 11/397,115 and in International Application No. PCT/IL06/001276, the contents of which are hereby incorporated by reference in their entireties. FIG. 3b depicts a fluid delivery device having a cradle 20 and a two-part dispensing unit 10, which employs, instead of a peristaltic pumping mechanism, a syringe-type pumping mechanism. A plunger 210 is displaced within a reservoir 220 and forces fluid towards the cannula 330. Further description of an arrangement such as the one shown in FIG. 3b is provided, for example, in co-owned, co-pending International Patent Application No. PCT/IL08/000641, filed May 11, 2008, claiming priority to U.S. Provisional Patent Application No. 60/928,815, filed May 11, 2007, the contents of both of which are hereby incorporated by reference in their entireties. Dispensing devices having other types of pumping mechanisms may also be used.

Figure 3C:
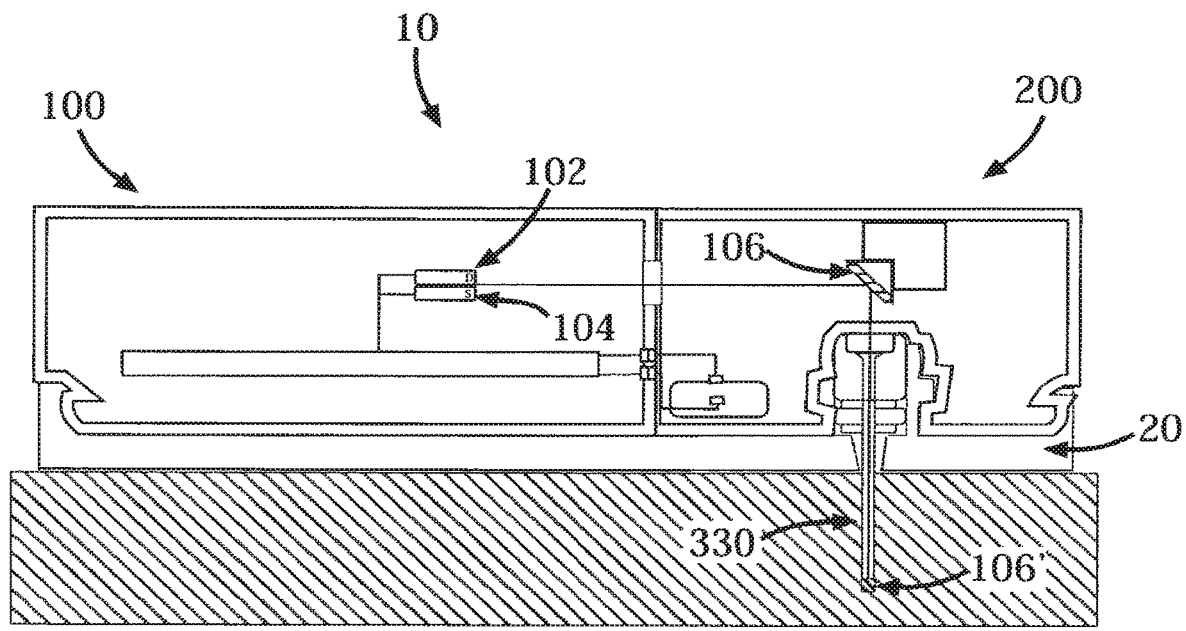

FIG. 3c illustrates an analyte sensing device that includes a two-part sensing unit 10 and a cradle 20. In some embodiments, an optical sensor for analyte sensing can be employed. One or more optical components 106 and 106' (e.g., reflectors, prisms, lenses, etc.) can be used to define an optical path between a light source 102 and a sample to be evaluated. In some embodiments, the optical path can be defined, at least partly, in the subcutaneous portion of the cannula 330. In some embodiments, the optical path terminates at a light detector 104. In general, light (e.g., visible light, IR radiation) is emitted from the source 102. The light is directed to the body via optical components 106 and 106' (through cannula 330). The light then interacts with the body's tissue (e.g., interstitial fluid), which comprises the sensed analyte (e.g., glucose). A portion of the light may be absorbed in and/or reflected from the analyte. As shown in FIG. 3c, reflected light is directed by optical components 106 and 106', from the body to the detector 104. Based on the reflected light characteristics, the analyte concentration level can be determined. Further description of embodiments similar to the arrangements depicted in FIG. 3a-c is provided, for example, in co-owned, co-pending U.S. patent application Ser. No. 11/989,678, filed Jan. 28, 2008, and International Patent Application No. PCT/IL07/001096, filed Sep. 5, 2007, both claiming priority to U.S. Provisional Patent Application No. 60/842,869, filed Sep. 6, 2006 and International Patent Application No. PCT/IL08/001520, the contents of all of which are hereby incorporated by reference in their entireties. Further description of embodiments employing electrochemical sensing mechanism is provided in U.S. patent application Ser. No. 11/989,665, filed Jan. 28, 2008 and International Patent Application No. PCT/IL07/001177, filed Sep. 25, 2007, both claiming priority to No. 60/848,511, filed Sep. 29, 2006, the contents of all of which are hereby incorporated by reference in their entireties.

Figure 3D:
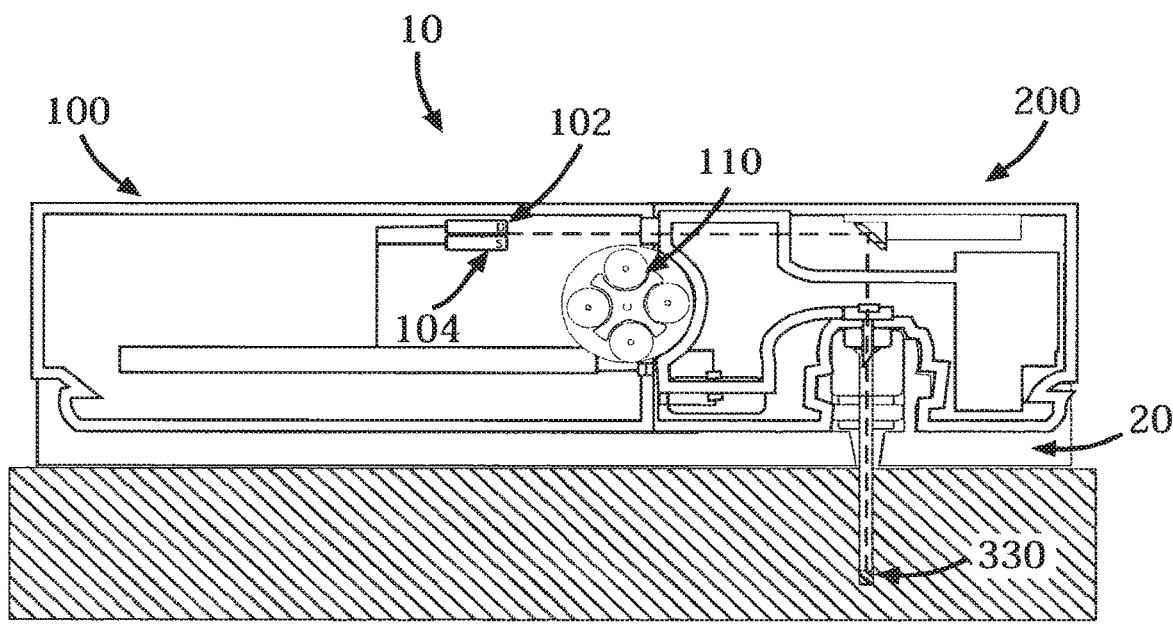

FIG. 3d illustrates a dual function device that includes a cradle 20 and a dispensing unit 10 configured to dispense therapeutic fluid (e.g., insulin) and sense analyte (e.g., glucose). This device can be configured to employ a single cannula that is used for both fluid delivery and analyte sensing operations. The dispensing and sensing functions may be performed independently from one another. Alternatively and/or additionally, the device may operate in a semi or fully closed-loop mode (i.e., fluid delivery operations may be based, at least in part, on the results of the sensed analytes). Additional description of an arrangement such as the one depicted in FIG. 3d is provided, for example, in a co-pending, co-owned U.S. patent application Ser. Nos. 11/706,606, 11/963,481, and International Patent Application No. PCT/IL08/001521, the contents of which are hereby incorporated by reference in their entireties.

In some embodiments, a sensor for measuring levels of bodily analytes (e.g., a continuous glucose sensor or monitor (e.g., CGM)) may be included in one housing, while the dispensing unit may be included in another housing(s). Thus, under those circumstances, the two units (e.g., the sensor and the dispensing unit) may be controlled and operated independently, and may communicate (e.g., wirelessly) directly or indirectly (e.g., via a remote control).

Figure 4:
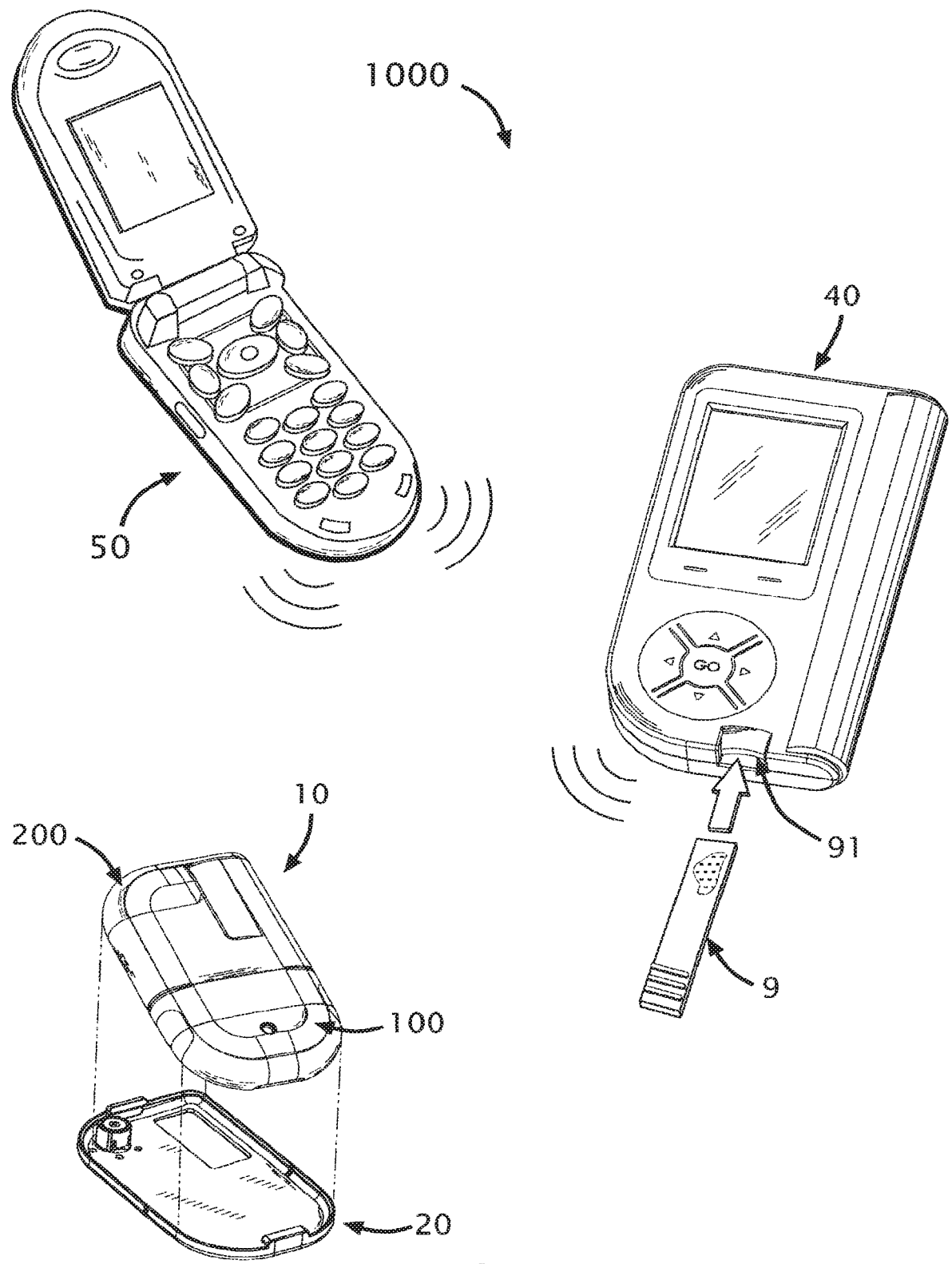
FIG. 4 is a diagram of a system that includes a dispensing unit, a remote control, a sensor unit and a cellular phone, that can all communicate with each other.

FIG. 4 is a diagram of a dispensing system 1000 according to some embodiments which is configured to enable communication between its various units/modules. Thus, as shown, the system 1000 includes a dispensing unit 10, a remote control 40, a sensor unit 9 and a cellular phone 50. The dispensing unit 10 may be configured to be connected/disconnected to and from a skin-securable (e.g., adherable) cradle 20. Each of the units depicted in FIG. 4 may communicate with one or more of the other units, and in some embodiments, with other units (e.g., PC, laptop).

As noted, in some embodiments, instructions/commands to control operations of the dispensing unit, as well as data (e.g., analyte level data) are communicated, for example, wirelessly, between the dispensing unit and a remote control. Communication of data and commands may become corrupted in an environment susceptible to interference (e.g., an environment that may include ambient interference, interference caused by transmission between other wireless devices, interference due to spatial distances between the remote control and dispensing unit). As described herein, to overcome interference that may cause corruption of communications and/or degrade the quality of transmission between individual units of the delivery device, the power and/or frequency of the transmission between the individual units of the dispensing device (e.g., the dispensing unit and the remote control) is set or adjusted based, in some embodiments, at least in part, on various parameters and conditions. For example, and as will become apparent below, transmission power may be increased to overcome RFI, or it may be reduced when the RFI level is low (e.g., to reduce power consumption). Alternatively and/or additionally, the transmissions parameters (e.g., transmission power, frequency, etc.) may differ based on the status of the unit. For example, an unpaired unit may transmit in a specific band which is different from the bands used by paired units. According to some embodiments, the transmission parameters may be adjusted periodically.

Figure 5A:
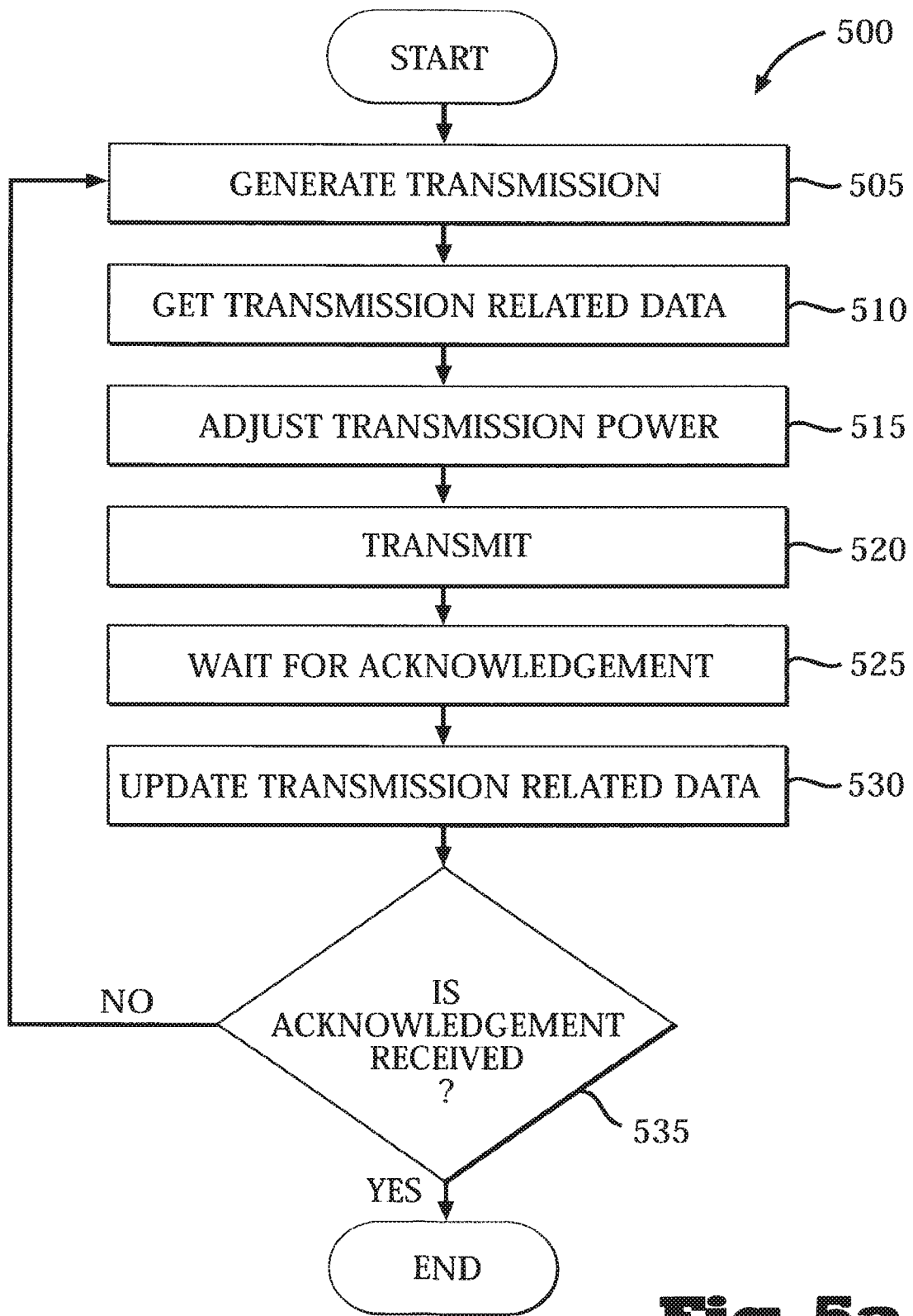

Referring to FIG. 5A and FIG. 5B, flowcharts of transmission power adjustment procedures at the transmitting and receiving units, are shown. Specifically, FIG. 5A depicts a procedure 500 performed by a transmitting unit of a dispensing device/system paired to a receiving unit of the device/system (e.g., a remote control or a dispensing unit having, among other things, an infusion pump to deliver therapeutic fluid to a body of a patient). Initially, the transmitting unit (e.g., the remote control) generates 505 a transmission message. Such a transmission message may include commands/instructions as well as data required to control fluid delivery operations, and may be transmitted using a suitable wireless communication protocol. In some embodiments, to determine the power that would be required to reliably transmit the message, transmission related data is obtained 510. This data may include one or more information items germane to reliable transmission, including, for example, historical data regarding the quality of transmission obtained in the course of communicating earlier messages, current information regarding possible level of interference (which may be obtained from one or more data sources that track communication activities), data particular to the units partaking in the transmission (e.g., physical distance between the units), etc.

Based on the transmission related data obtained, the power level that would be required to reliably transmit the generated transmission message may be either determined 515 or a pre-determined power level is adjusted (also at 515), e.g., adjusting some default power level used as an initial guess/estimation for the power level to be used. Determination or adjustment of the transmission power level may be performed based, for example, on predetermined data (e.g., stored in tables) that relates the transmission related data to corresponding power levels that should be used. Alternatively and/or additionally, mathematical relationships relating the required power level as a function of parameters/conditions corresponding to the transmission related data (i.e., the data obtained, for example, at 510) may be used to compute the required power level.

Having determined or adjusted the power level required for a reliable transmission, the generated transmission message may then be transmitted 520. As noted, transmission of the message may be based on a suitable communication protocol, and may include pre- and post processing to increase the likelihood of transmitting the message without corruption. Details regarding communication protocols and various communication processing operations that may be performed on the generated message are provided, for example, in the International Patent Application No. PCT/IL08/000842, entitled "COMMUNICATIONS FOR MEDICINAL FLUID DELIVERY SYSTEM", which claims priority from provisional application Ser. No. 60/936,726, also entitled "COMMUNICATIONS FOR MEDICINAL FLUID DELIVERY SYSTEM", the contents of all of which are hereby incorporated by reference in their entireties.

In some embodiments, once the message has been transmitted, the transmitting unit optionally waits 525 for an acknowledgment from the recipient (destination) unit to indicate that the receiving unit has received the transmitted message. If an acknowledgement signal is not received within a pre-determined period of time, as determined in 535

(thus indicating that the receiving unit has not received the message, has received a corrupted version of the message, or that the power level of the acknowledgement message is too low), the transmitting unit (in some embodiments) repeats the operations 510-535. Specifically, at 510 the transmitting unit obtains transmission related data which at this point may include data representative of the failure of the receiving unit to send an acknowledgement in response to the earlier attempt by the transmitting unit to transmit the generated message. Such data may have been updated at 530.

Thus, the updated data relating to the transmission will cause a re-adjustment, at 515, of the power level to be used to transmit the message. Here too, the re-adjustment may be based on using pre-determined data related to the occurrence or existence of certain conditions (e.g., failure to acknowledge receipt of a transmitted message) to the required power level. Alternatively and/or additionally, the power level required to transmit the message may be adjusted in correspondence with some pre-determined level (e.g., a 5% increase relative to the previous transmission). After re-adjustment of the power level, the message may be re-transmitted, at 520, and the operations of waiting 525 for an acknowledgement, updating 530 the data related to the transmission, etc., are repeated. In some embodiments, a re-transmitted message may include data to instruct the receiving unit to increase the power level of subsequently sent acknowledgement messages if it is determined that the failure to receive an acknowledgement may have resulted from the power level of an earlier sent acknowledgement message(s) being too low.

FIG. 5*b* is a flowchart of a procedure 550 depicting operations performed by a receiving unit in the course of determining/adjusting the power level required to established a reliable communications link between the transmitting and receiving units of a fluid delivery device, according to some embodiments. As shown, a receiving unit (e.g., the dispensing unit that includes a pumping/infusion mechanism, or alternatively, the remote control) waits 560 for receipt of a message transmission from a transmitting unit. The receiving unit can wait for transmission by monitoring/listening some of the time (periodically and/or randomly) and/or all of the time (i.e., continuously) to the ISM bands, for example. The receiving unit receives 565 the message transmission, and based on the received message, the receiving unit updates 570 transmission related data. For example, in some embodiments, the receiving unit processes the message to determine if, and to what extent, the content of the message has been corrupted. For example, error-check codes and/or error-correction codes, such as checksum codes, cyclic-redundancy-check codes (CRC), forward error correction (FEC), etc., may have been added to the content of the message to enable determination of the occurrence of transmission corruptions. Additionally, the receiving unit may determine other data related to the received transmission, including the signal-to-noise ratio (by comparing, for example, the received data to known and/or anticipated data that was supposed to be included with the transmitted message). Other types of transmission related data may also be determined or otherwise obtained by the receiving unit. The transmission related data may be stored on a storage device (e.g., a memory) included in, or coupled to, the receiving unit.

The receiving unit can send 575 an acknowledgement message to the transmitting unit that may include the transmission related data obtained based on receipt of the transmission message from the transmitting unit. In some embodiments, the transmission related data determined or obtained by the receiving unit may be used to update a data repository, e.g., a database on a remote server, that is available to a user or caregiver overseeing the power adjustment procedure, to the transmitting and/or to the receiving units so that both units may make necessary adjustments to, for example, the transmission power level. In some embodiments the receiving unit may request the transmitting unit to alter its Power of Transmission (POT) and/or other transmission parameters, for example, after receiving message having a pre-determined number of errors, and/or after receiving a predetermined number of corrupted messages.

Adjustment of the transmission power may be performed at various stages during the interaction between the individual units of, for example, a fluid dispensing device. For example, the transmission power adjustment procedure may be performed during performance of a pairing procedure between the units of the device (e.g., when the linking between the individual units is being established). During the pairing procedure, the transmission range of at least one of the units may be reduced to allow communication only over a short range, thus minimizing the chance for mispairing (e.g., pairing a dispensing unit of one user with a remote control unit of another user). In some embodiments, unpaired units initial transmission may be performed at a limited range and/or power. For example, the range of communication during pairing may be less than 50 cm. In some embodiments, after the pairing procedure is completed, the transmission power used to communicate between the paired units may be increased.

Transmission power adjustment may also be performed during regular wireless communication operations between a device's units, e.g., during typical usage of the dispensing device when commands/instructions are transmitted to a dispensing unit, when data regarding the dispensing device operation is transmitted from the dispensing unit and/or the remote control, to transmit user information, health related data, etc. As noted, the Power of Transmission (POT) can be adjusted based on received massages, RPI determination, indications from another unit of the device or from external sources. For example, during normal operations, RPI can be measured before transmission of a particular message and the POT used for transmitting will be determined or adjusted accordingly. Determining the transmission power may thus be based on RFI level, determination of whether a received massage includes error and/or missing data (indicating a power increase may be required), the amount/percentage of corrupted transmissions, Signal-to-Noise Ratio (SNR), the transmission power of received messages, Received Signal Strength Indication (RSSI), etc.

In some embodiments, a tailored transmissions procedure may be implemented to determine an optimal transmission power (e.g., the minimal power level that provides reliable transmission). In some embodiments, a particular message(s) may be transmitted in various POTs (for example, POTs covering a range or higher and lower power levels), and the minimal POT or near minimal POT in which the quality of transmission is deemed acceptable is identified.

In some embodiments, the POT may be adjusted according to the messages types (e.g., bolus delivery, pause delivery, time synchronization) and/or the message contents (e.g., the amount of fluid to be delivered, number of corrupted messages). For example, messages related to fluid delivery suspension (or other types of messages containing critical data) may be transmitted in the maximum POT, regardless of the POT applied to other transmissions.

Figure 6:
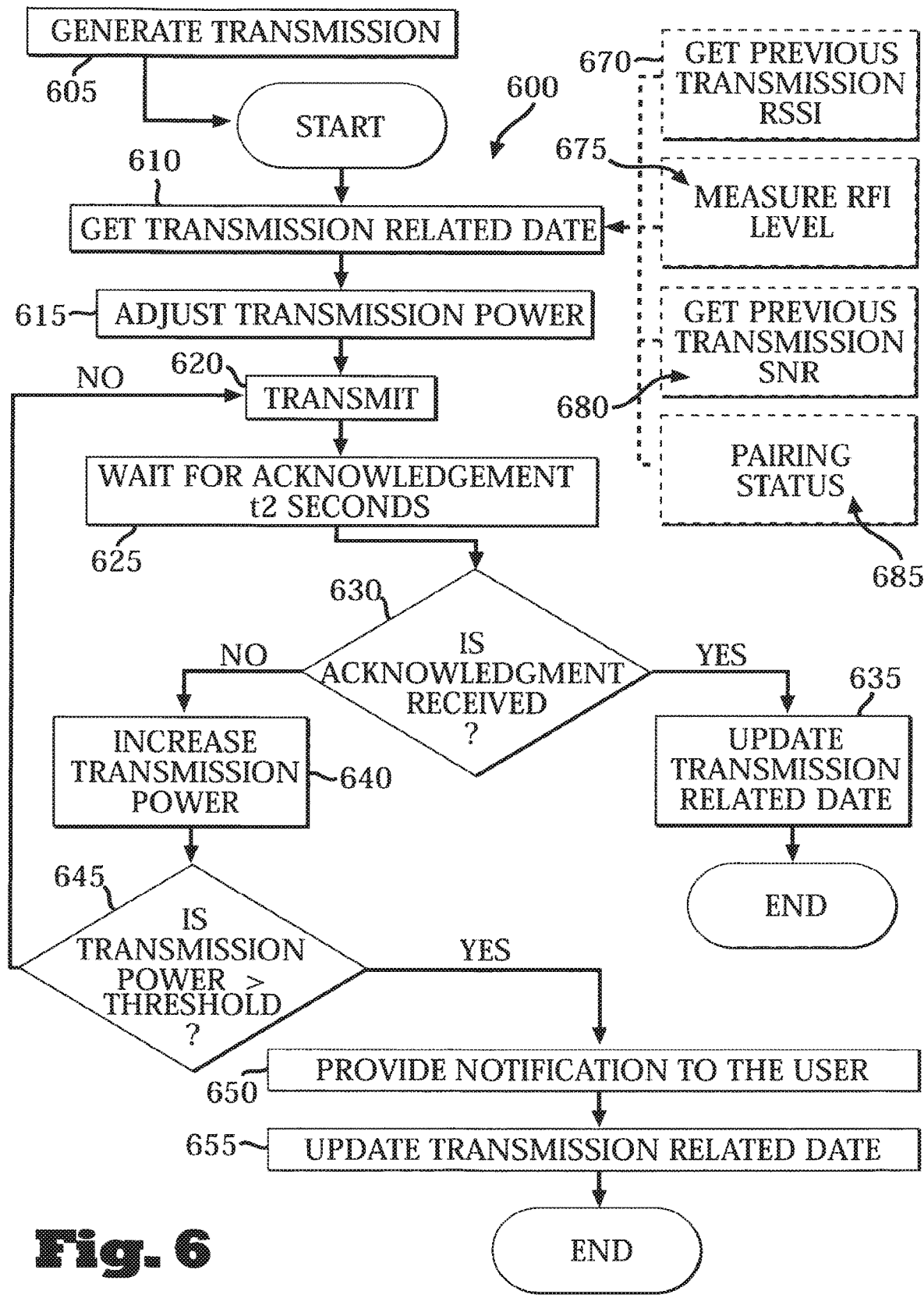
FIG. 6 is a flowchart of a process for adjusting transmission power.

Referring to FIG. 6, a flowchart of a power setting/adjustment procedure 600 according to some embodiments is shown. As with the procedure 500, initially, a transmission message is generated 605. Such a transmission message may include a test message with a pre-determined format and content to enable determination of the communication conditions (e.g., level of interference) and thus enable determination of the transmission power requirements. Having generated the transmission message, transmission related data is obtained 610 by, for example, performing measurements to determine one or more transmission related values (e.g., parameters and/or conditions) pertaining to reliably transmitting messages and/or parameters and conditions pertaining to the expected or existing level of interference. Transmission related data may also be obtained by receiving transmission related data from another (e.g., external) source (e.g., from the other unit with which the current transmission unit is communicating, from a data repository that the current transmission unit has access to, etc.).

As further shown in FIG. 6, several types of data may be obtained and/or determined. For example, the Received Signal Strength Indication (RSSI) information relating to the previous transmission(s) that may have taken place between the transmitting and receiving unit (or some other combination of communicating units) may optionally be obtained 670. For example, in response to a previous transmission sent by the transmitting unit to the receiving unit with which it is paired, the receiving unit may have sent a reply message/signal indicating the signal strength of the transmission it received. Based on the RSSI data, the power level may be adjusted. For example, if the RSSI is too low, this may be indicative of considerable interference necessitating an increase of the transmission power level. In some embodiments, another data that may be obtained or determined is the radio frequency interference (RFI) level (at 675). For example, a detector may be used to measure the power levels at various frequencies (e.g., over some frequency range in which transmissions from the transmitting unit will take place). Another type of data that may optionally be obtained 680 is the previous transmission's signal-to-noise ratio (SNR). A further type of data that may be obtained 685 is the unit's pairing status information, e.g. whether the transmitting unit is paired and/or about to be paired to another unit.

As in procedure 500, after obtaining or determining data germane to reliable communication transmissions, the transmission power to be used for transmitting the generated message can be determined or adjusted 615. The transmission power level may be determined/adjusted based, at least in part, on the transmission related data obtained at 610. For example, if the SNR of the previous transmission (e.g., as determined at 680) is deemed to be too low, thus indicating large level of interference and/or corruption, the transmission power may be adjusted so as to increase the power level. In some embodiments, determination or adjustment of the power level may be performed using a mathematical formula relating the required power level as a function of, for example, the transmission related data (e.g., the data obtained at 610).

After adjusting the transmission power, the generated message is transmitted 620, and the transmitting unit then waits 625 for an acknowledgement signal to be received. In some embodiments, the transmitting unit waits for a pre-determined period of time (designated $t_2$). If within that time period the transmitting unit receives an acknowledgement from the receiving unit, the transmission related data is updated 635. The data that may be used to update the transmission related data may include data contained within the acknowledgement signal, including the SNR and RSSI of the just completed transmission, the fact that the receiving unit did receive the transmitted message and was able to respond thereto, etc.

If, on the other hand, an acknowledgement was not received within the time period $t_2$ (as determined at 630), thus indicating that the transmission may not have been received due to excessive interference, the transmission power level is increased 640. The new increased power level may be compared 645 to a pre-determined power level threshold representing the maximum allowable transmission power, and if the newly adjusted power level has not yet exceeded that threshold, then the operations commencing at 620 are repeated. On the other hand, if the increased power level exceeds the pre-determined threshold, a notification to that effect is provided to a user 650 (e.g., a patient, a technician, a caregiver, etc.), and the transmission related data is updated 655 (e.g., quantitative data pertaining to the SNR, RSSI, etc., as well as data to reflect the fact that the maximum allowable transmission power has been reached but that reliable transmission of data has not yet been achieved).

In some embodiments, to establish reliable communication, the frequencies in which messages are transmitted may be set or adjusted. Setting or adjustment of the transmission frequencies may be performed during pairing of two or more units (e.g., pairing of a remote control and a dispensing unit of an infusion/dispensing device), after a certain pre-determined time period has elapsed (e.g., every 30 seconds, every 1 hour, every day, etc.), in response to event that indicates that frequency adjustment should be performed to maintain reliable communication (e.g., if a transmitting unit has received, at a particular frequency, transmissions from a unit associated with another device, thus indicating that there are multiple devices using the same frequency to transmit messages), and/or when other types of communication problems are detected.

Figure 7A:
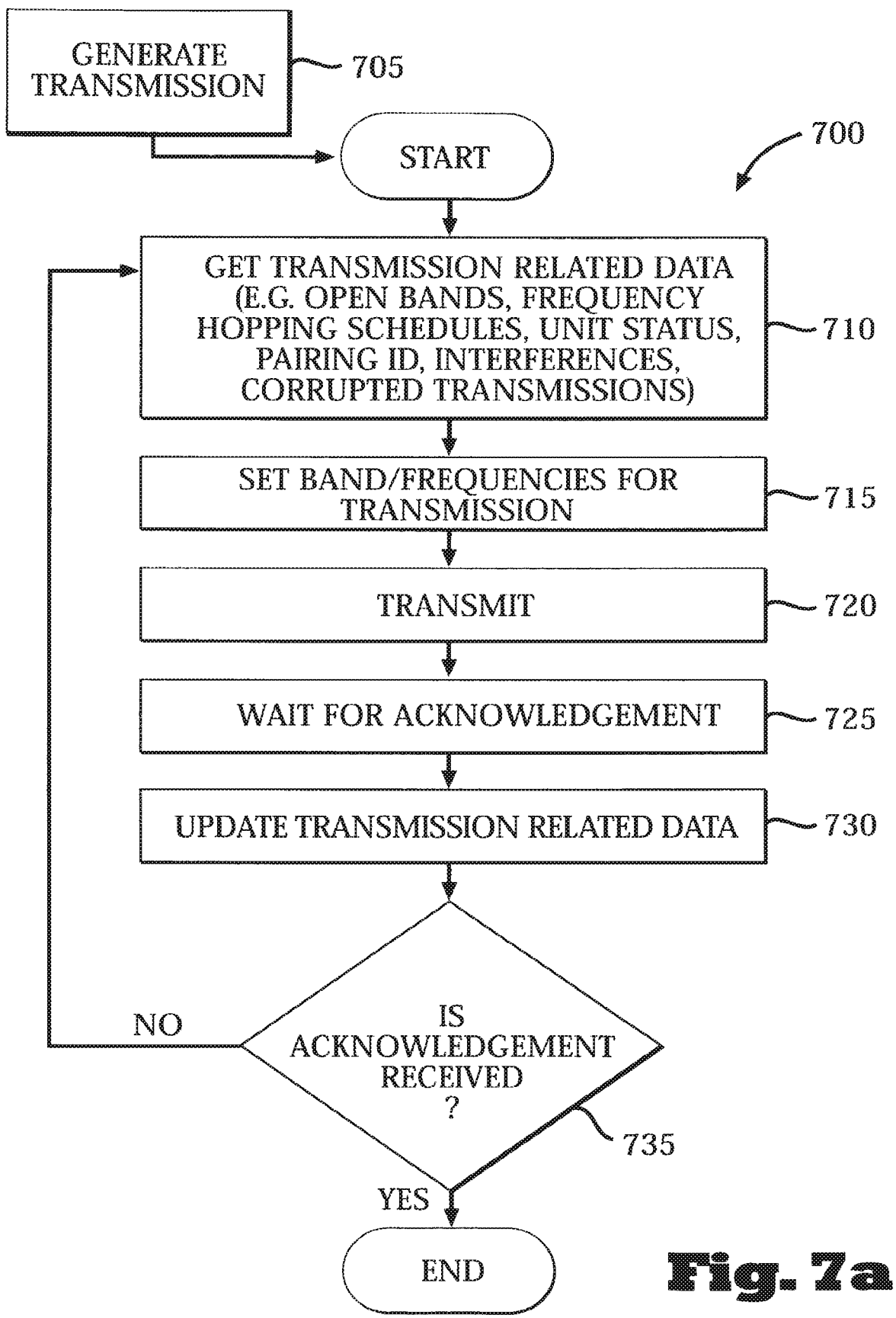
FIGS. 7a-b are flowcharts of processes for adjusting bands and/or frequencies for transmission, at the transmitting part (FIG. 7a) and at the receiving part (FIG. 7b).
Figure 7B:
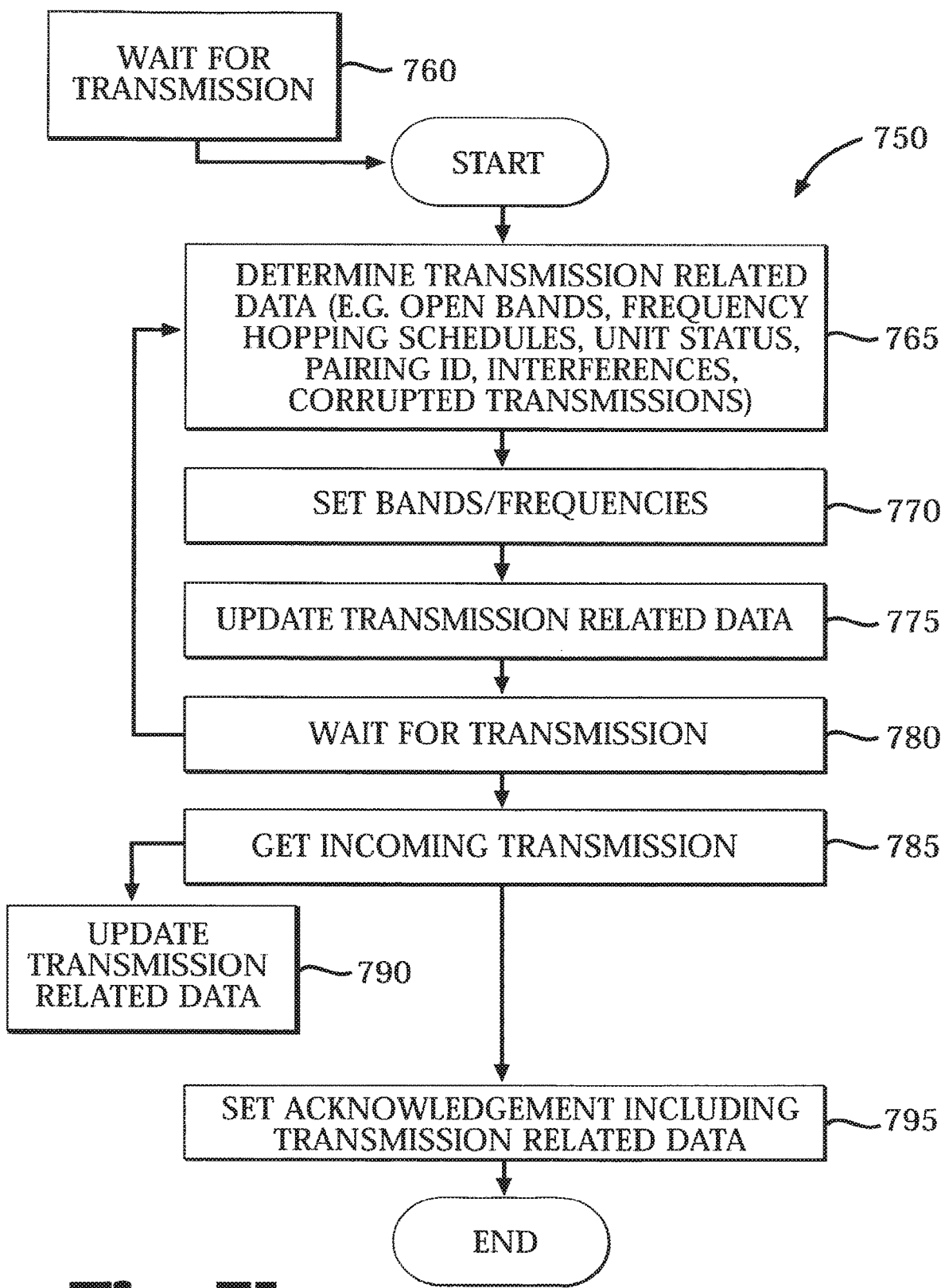

Referring to FIGS. 7a-b, flowcharts of procedures to adjust transmission bands and/or frequencies for transmission, at the transmitting part (FIG. 7a) and at the receiving part (FIG. 7b) are shown. FIG. 7a depicts a procedure 700 to set/adjust the frequency used for transmission. A transmitting unit (e.g., a remote control unit) first generates 705 a message which, as similarly described in relation to the procedures 500 and 600, may be a test message that includes some specific pre-determined content and which has known predetermined characteristics (for example, the message may be transmitted at a particular initial frequency).

Having generated the message, transmission related data is obtained 710. As more particularly described in relation to FIG. 8, transmission related data may include the various open bands (e.g., available bands not currently used by other devices for transmission), frequency hopping schedule and level of interference at various frequencies (e.g., respective SNR, SRRI, etc., at the various frequencies). Additional data relating to transmission of messages between the transmitting and receiving unit(s) may include data regarding corrupted transmissions (e.g., to what extent previous transmissions between the units in question have been corrupted), and also data regarding the units' status (e.g., normal operation, unpaired, waiting/during pairing).

Based, at least in part, on the transmission related data obtained, the band or frequency to use for transmission of the generated message is determined and set 715. For example, if it is determined, during the data gathering operation at 710, that certain transmission frequencies are available and/or that data integrity at those frequencies/band is adequate (e.g., data corruption was deemed to be relatively limited), one or more of those frequencies may be used for transmission of the generated message. Thus, after setting the band/frequency, the generated message is transmitted 720. The transmitting unit then waits 725 for an acknowledgement from the receiving unit. If no acknowledgement was received (as determined at 735), thus indicating that communication on the set band/frequency is unreliable, the operations 710-735 are repeated to determine and to set a different band/frequency with which to transmit the message. The procedure 700 may be repeated until a suitable band/frequency is determined or until a time-out or termination criterion is met (e.g., no suitable band/frequency is identified after a determined number of tries). During performance of the procedure 700, data relating to the transmission is updated 730. Such data updating may include updating a central data repository, or updating the transmitting unit itself, with data representative of the quality of the transmission at the current set band/frequency, and may also include data representative of success or failure of the transmission (e.g., if no acknowledgement is received from the receiving unit, this may indicate that the current band/frequency may not be suitable for reliable transmission).

FIG. 7b is a flowchart of an exemplary procedure 750 depicting operations performed by a receiving unit in the course of determining/adjusting the band/frequencies required to establish and/or maintain a reliable communications link between the transmitting and receiving units of, for example, a fluid delivery device. Similar to the operations undertaken by a receiving unit (be it a dispensing unit or a remote control) in relation to the power adjustment procedures of FIGS. 5a-b, here too a receiving unit waits 760 for receipt of a message transmission from a transmitting unit. In some embodiments, the various units of a particular device may not be synchronized. For example, the units may not have a priori established which frequencies will be used to communicate. Thus, the receiving unit may not have determined on which frequency (or frequencies) the transmitting unit is expected to be sending the transmissions. Accordingly, the receiving unit may first determine 765 transmission related data (independently from any such determination performed by the transmitting unit) to determine open bands, interference data, band available for spread spectrum, pairing ID data, unit status, and data regarding corrupted information. Based on that determination, the receiving unit sets 770 its receiving frequency (e.g., adjusting or tuning its receiver or transceiver to the determined frequency) and updates 775 transmission related data. Alternatively and/or additionally, the receiving unit may listen to a wider frequencies range and/or to wait for wideband transmission. The receiving unit then waits 780 to receive transmissions sent by the transmitting unit. Failure to receive a transmission from the transmitting unit may be indicative that the particular frequency set by the receiving unit may not be suitable for transmission (e.g., there is excessive interference on the currently selected frequency) or that the units attempting to communicate are not using the same frequency. Thus, if the receiving unit did not receive a transmission within a pre-determined period of time, the receiving unit repeats the operations 765-780. Particularly, a new frequency or band is determined, taking into account, in some embodiments, the fact that a communication link was not established on the previously set frequency.

If a transmission is received 785, data relating to the transmission, including, for example, the fact that the transmission was received, metrics relating to the transmission (e.g., level of message corruption), etc., is updated 790. In addition, the receiving unit also sends 795 an acknowledgement to the transmitting unit, including transmission related data. In some embodiments, the transmission related data determined or obtained by the receiving unit may be used to update a data repository, e.g., a database on a remote server to enable the transmitting and the receiving units to make necessary adjustment to, for example, the frequency/band used.

In some embodiments the receiving unit may request the transmitting unit to change frequency and/or other transmission parameters, for example after receiving message with pre-determined errors, and/or after receiving predetermined number of somewhat corrupted messages.

Figure 8:
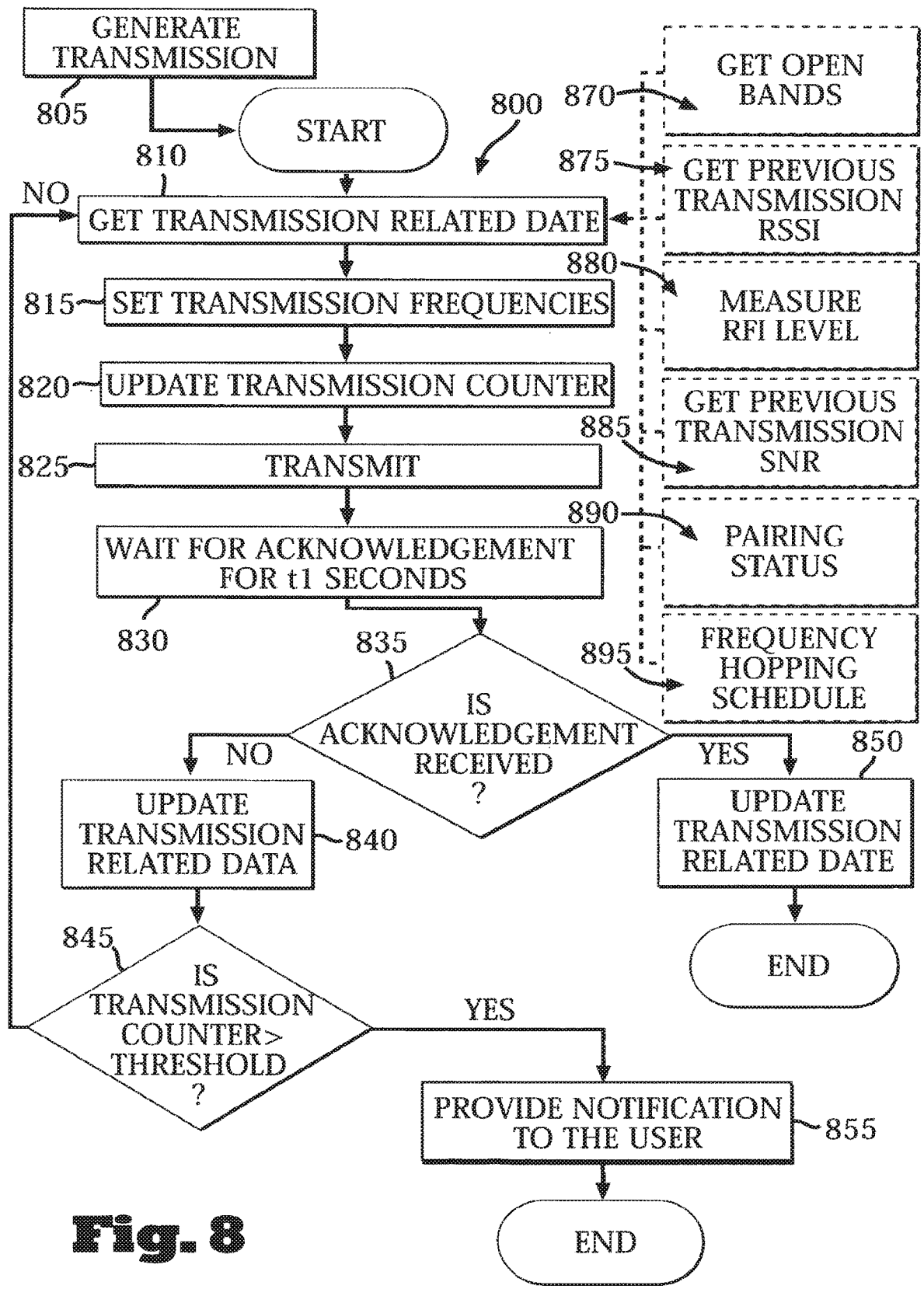
FIG. 8 is a flowchart of a process for adjusting bands and/or frequencies for transmission.

Referring to FIG. 8, a flowchart of a frequency setting/adjustment procedure 800 is shown. As with procedure 700, initially, a transmission message is generated 805. Such a transmission message may include a test message with a pre-determined format and content to enable determination of the communication conditions (e.g., level of interference) and thus enable determination of suitable frequencies. Having generated the transmission message, transmission related data is obtained 810 by, for example, performing measurements to determine one or more transmission related values (e.g., parameters and/or conditions) pertaining to transmitting messages and/or expected or existing level of interference. Transmission related data may also be obtained by receiving transmission related data from another (e.g., external) source (e.g., from the other unit with which the current unit is communicating, from a data repository that the current unit has access to, etc.).

As further shown in FIG. 8, several types of data may be obtained and/or determined. For example, the Received Signal Strength Indication (RSSI) information relating to the previous transmission that may have taken place between the transmitting and receiving unit (or some other combination of communicating units) may optionally be obtained 875. For example, in response to a previous transmission sent by the transmitting unit to the receiving unit, the receiving unit may have sent a reply message/signal indicating the signal strength of the transmission it received. Based on the RSSI data, the frequency or band may be adjusted. For example, if the RSSI is too low, this may be indicative of considerable interference necessitating a change of the frequency used for transmission.

In some embodiments, another type of data that may be obtained or determined is the radio frequency interference (RFI) level (at 880). For example, a detector may be used to measure the power levels at various frequencies (e.g., over some frequency range in which transmissions from the transmitting unit will take place). Another type of data that may optionally be obtained 885 is the previous transmission's signal-to-noise ratio (SNR). Yet another type of data that may be obtained 890 is the pairing status information. Other types of data that may optionally be obtained include data pertaining to the various open bands or frequencies that may be available (obtained at 870), and frequency hopping schedule(s) (obtained at 895). Other types of data may also be obtained.

After obtaining or determining data germane to the band/frequencies that may be used to establish reliable communication between distributed units of the device, the transmission frequency(ies) to be used are set 815. The transmission frequency(ies) may be determined/adjusted based, at least in part, on the transmission related data obtained at 810. For example, if the SNR of the previous transmission was determined (e.g., at 885) and deemed to be too low, possibly indicating large level of interference and corruption, another frequency that may possibly be less susceptible to interference may be chosen.

A transmission counter is updated 820 and the generated message is transmitted 825. The transmission counter is used to keep track of how many different types of bands/frequencies have been examined in the course of identifying a band/frequency suitable for reliable communication between the units of the particular device. After transmission of the message, the transmitting unit waits 830 for an acknowledgement signal to be received. In some embodiments, the transmitting unit waits for a pre-determined period of time (designated t,). If within that time period the transmitting unit receives an acknowledgement from the receiving unit (as determined at 835), the transmission related data is updated 850. The data that may be used to update the transmission related data may include data contained within the acknowledgement signal, including the SNR and RSSI of the just completed transmission, the fact that the receiving unit did receive the transmitted message and was able to respond thereto, etc.

If, on the other hand, an acknowledgement is not received within the time period t\, thus indicating that the transmission may not have been received due to excessive interference, or lack of synchronization between the individual units of the device, the transmission related data is updated 840 accordingly, and a determination is made 845 whether the transmission counter has reached a pre-determined threshold value. If the counter value exceeds the threshold value, thus indicating that the number of permissible communication linking attempts has been reached, an appropriate notification is provided 855 to the user. If the number of transmission attempts has not yet reached the pre-determined threshold value, the operations commencing at 810 are repeated.

Figure 9:
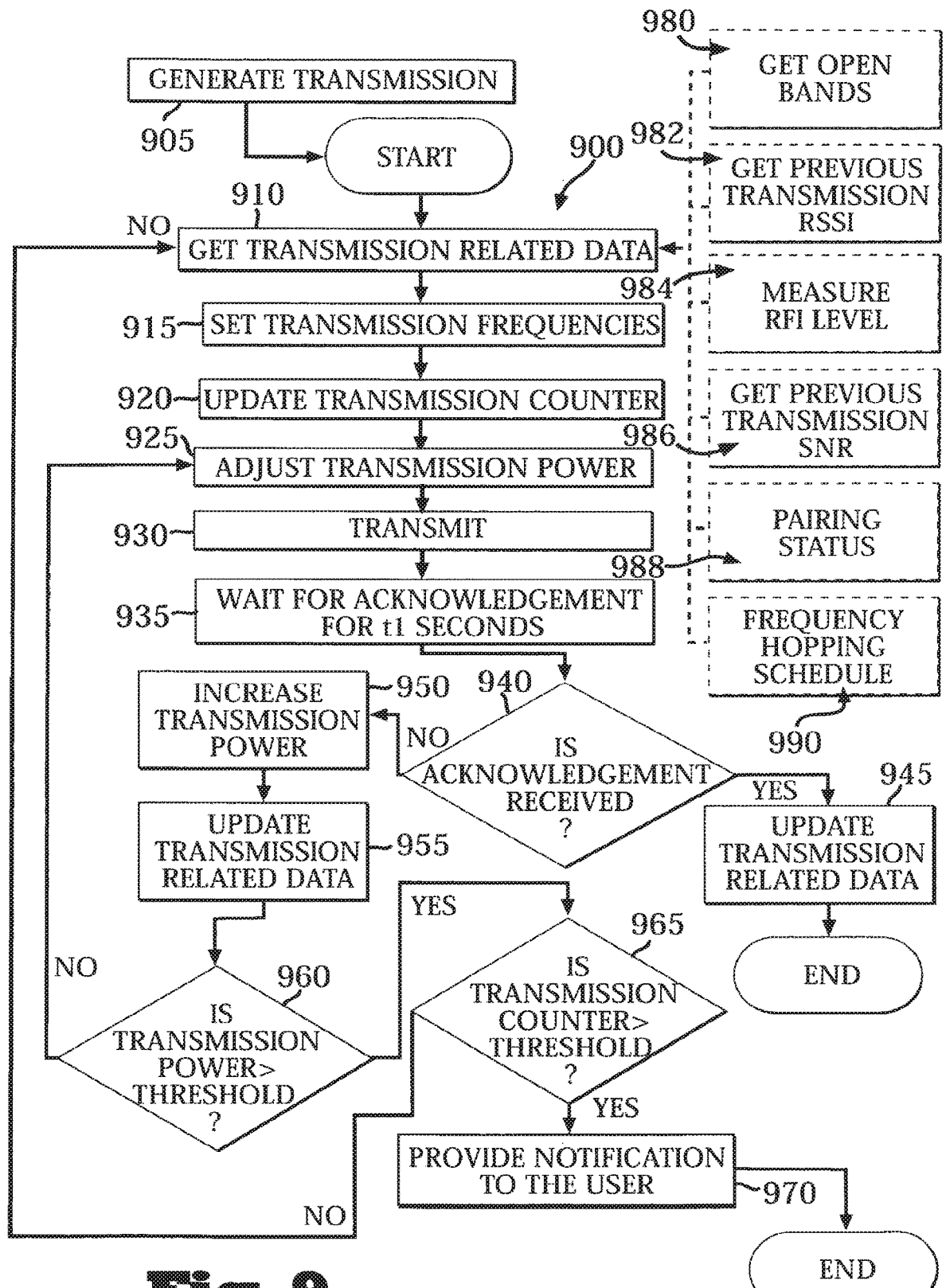
FIG. 9 is a flowchart of a process for adjusting transmission power, bands and/or frequencies for transmission.

Referring to FIG. 9, a flowchart of a transmission setting procedure 900 is shown. The procedure 900 includes operations to determine/adjust the power and frequency attributes of communication transmissions (e.g., wireless communication transmissions) between units of a device such as a fluid dispensing device. However, operations to determine/adjust other transmission attributes may also be included. As will be described below, in some embodiments, the implemented operations may be similar to the operations implemented with respect to procedures 600 and 800 depicted in FIGS. 6 and 8, respectively.

In some embodiments, the transmission attribute determination/adjustment procedure seeks to identify for a particular frequency the power level that would result in reliable communication. If, in these implementations, a suitable power level that would result in reliable communication cannot be determined, a different frequency is used to determine if for that new frequency a power level resulting in reliable communication can be found.

In some embodiments, one of the units operates as a master, and thus this unit notifies the other unit what frequency(ies) to use and/or what is the required POT. Additionally and/or alternatively, one of the unit accumulates the transmission related data and provides it to the other unit(s) of the dispensing device. In some embodiments, one unit notifies the other unit which frequencies and/or POT to apply for transmission.

Thus, as shown in FIG. 9, initially, a transmission message is generated 905 (e.g., a test message with a pre-determined format and/or content to enable determination of the communication conditions). Transmission related data is then obtained 910 by, for example, performing measurements to determine one or more transmission related values (e.g., parameters and/or data indicative of conditions) pertaining to transmitting messages and/or parameters and conditions pertaining to the expected or existing level of interference. Transmission related data may also be obtained by receiving transmission related data from another (e.g., external) source (e.g., from the other unit with which the current unit is communicating, from a data repository that the current unit has access to, etc.). As with procedure 800, several types of data may be obtained and/or determined, including, for example, the Received Signal Strength Indication (RSSI) information relating to the previous transmission (at 982). Under such circumstances, in response to a previous transmission sent by the transmitting unit to the receiving unit with which it is paired, the receiving unit may have sent a reply message/signal indicating the signal strength of the transmission it received. Based on the RSSI data, the frequency/band and/or the transmission power may be adjusted. Other types of data that may be obtained or determined include the radio frequency interference (RFI) level (at 984), the previous transmission's signal-to-noise ratio (SNR), at 986, the pairing status information (at 988), open bands information and/or frequencies that may be available for communication transmission (obtained at 980), and frequency hopping schedule(s) (obtained at 990). Other types of data may further be obtained.

In some embodiments, the transmission related data of the transmitting unit is kept in the receiving unit (e.g., in a memory). In some embodiments, the transmission related data is kept in the transmitting unit. In a bi-directional communication both units may act as a transmitting unit and/or as a receiving unit, simultaneously and/or alternately.

After obtaining or determining data germane to the band/frequencies and transmission power (and/or data germane to other transmission attributes) which may be used to establish reliable communication between units of the device, the transmission frequency(ies) to be used are set 915, and a transmission counter to keep track of how many different types of bands/frequencies have been examined in the course of determining the various transmission attributes is updated 920 (e.g., setting the counter to 0 or 1). The transmission frequency(ies) is determined/adjusted based, at least in part, on the transmission related data obtained at 910.

Subsequently, the transmission power to be used for transmitting the generated message is determined or adjusted 925. As with the band/frequency to be used, the transmission power level may be determined/adjusted based, at least in part, on the transmission related data obtained at 910. For example, if the SNR of the previous transmission was determined (e.g., at 986) and deemed to be too low (e.g., the SNR is indicative of large interference and corruption levels), the transmission power may be adjusted so as to increase the power level. As noted, in the implementations depicted in FIG. 9, various power levels are checked for a particular frequency to determine if a suitable power level exists that would result in reliable transmission at the given frequency, and if so, further checks for reliable transmissions at other frequency need not be performed. However, in some embodiments, determination of the transmission attributes may be performed by determining if reliable communication transmissions can be achieved for a particular power level. That is, in such implementations, various frequencies are tested with respect to a particular power level. Other schemes for determining appropriate transmission attributes may be employed.

Turning back to FIG. 9, after setting or adjusting the transmission power level, the message is transmitted 930.

The transmitting unit then waits 935 for an acknowledgement to be received. In some embodiments, the transmitting unit waits for a pre-determined period of time (designated $Z_1$). If within that time period the transmitting unit receives an acknowledgement from the receiving unit (as determined at 940), the transmission related data is updated 945. As with procedure 800, the data that may be used to update the transmission related data may include data contained within the acknowledgement signal, including the SNR and RSSI of the just completed transmission, the fact that the receiving unit did receive the transmitted message and was able to respond thereto, etc.

If, on the other hand, an acknowledgement was not received within the time period t\, thus indicating that the transmission may not have been received due, for example, to excessive interference, etc., the transmission power level is increased 950, and the transmission related data is updated 955. The new increased power level is compared 960 to a pre-determined power level threshold representing the maximum allowable transmission power, and if the newly adjusted power level has not yet exceeded that threshold, then the operations commencing at 925 are repeated (i.e., to examine the reliability and quality of transmission with the new power level, using the current set frequency/band).

If the transmission power used for to transmit the message at the current set frequency exceeds the pre-determined power threshold, then a determination is subsequently made 965 as to whether the transmission counter has reached a pre-determined threshold value. If the counter value exceeds the threshold value, thus indicating that the number of permissible communication linking attempts has been reached, an appropriate notification is provided 970 to the user. If the number of transmission attempts has not reached the pre-determined threshold value, the operations commencing at 910 are repeated to determine transmission attributes for a new frequency or band. Selection of the new frequency or band to examine may be performed with reference to a list or table identifying the various frequencies that may be tested, and the order in which to test them. Alternatively and/or additionally, the frequency selection may be performed by incrementing or decrementing the current frequency value by a pre-specified frequency value (e.g., try frequency at intervals of 10 KHz), or by performing any other frequency selection procedure (e.g., using mathematical relationships to determine a frequency to be tested based, for example, on the values of one or more of the parameters and conditions determined at 980-990).

Various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. Some embodiments include specific "modules" which may be implemented as digital electronic circuitry, integrated circuitry, specially designed ASICs (application specific integrated circuits), computer hardware, firmware, software, and/or combinations thereof.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flows depicted in the accompanying figures and described herein do not require the particular order shown, or sequential order, to achieve desirable results.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

What is claimed is:

1. A method for adaptive wireless communication transmissions between units of an ambulatory portable medical device, the method comprising:
    obtaining transmission quality data relating to one or more prior wireless transmissions between the units of the medical device; and
    setting one or more attributes of a wireless transmission of one or more messages between the units of the medical device based, at least in part, on the obtained transmission quality data, wherein the one or more attributes of the wireless transmission include a transmission power level and at least one of a first frequency and a first band determined based on the obtained transmission quality data;
    wirelessly transmitting a message at a first power level using the one or more attributes of the wireless transmission;
    increasing the transmission power level to a second power level at the at least one of the first frequency and the first band upon an acceptable acknowledgement in response to the transmission is not received such that an acknowledgement in response to the transmission is not received within a predetermined time period or upon the acknowledgement is received but includes a pre-determined number of errors or a predetermined numbers of corrupted messages;
    wirelessly transmitting the message at the second power level; and
    comparing the second power level to a maximum power level threshold and, upon the second power level threshold exceeding the maximum power level threshold, determining one or more additional power levels at least one of a second, different frequency and a second, different band until the acknowledgement in response to the transmission is received or a pre-determined threshold counter value indicative a number of permissible communication linking attempts has been reached.

2. The method of claim 1, further comprising:
    communicating the one or more messages between a first unit and a second unit of the medical device via wireless transmission configured with the one or more attributes.

3. The method of claim 1, further comprising:
    in response to receiving the one or more messages transmitted, sending an acknowledgement, by the other of the units of the medical device, to the one of the units of the medical device.

4. The method of claim 1, wherein setting the one or more attributes of the wireless transmission of the one or more messages comprises:
    determining at least one frequency of the wireless transmission of the one or more messages based on the obtained data.

5. The method of claim 4, further comprising:
    transmitting the one or more messages at the at least one determined frequency from one of the units of the medical device to another of the units of the medical device.

6. The method of claim 5, further comprising:
    in response to receiving the one or more messages transmitted, sending an acknowledgement, by the other of the units of the medical device, to the one of the units of the medical device.

7. The method of claim 5, further comprising:
    determining at least one other frequency upon a determination that an acknowledgement responsive to the transmitted one or more messages was not received.

8. The method of claim 1, wherein setting the one or more attributes of the wireless transmission of the one or more messages comprises:
    determining a power level and at least one frequency of the wireless transmission of the one or more messages based on the obtained data.

9. The method of claim 8, further comprising:
    transmitting the one or more messages at the at least one determined frequency and the determined power level from one of the units of the medical device to another of the units of the medical device.

10. The method of claim 9, further comprising:
    performing one of determining another frequency and increasing the power level upon a determination that an acknowledgement responsive to the transmitted one or more messages was not received.

11. The method of claim 1, wherein the medical device includes a therapeutic fluid dispensing device and wherein setting one or more attributes of the wireless transmission of the one or messages comprises:
    setting one or more attributes of the wireless transmission between two or more of: a remote control to control at least some of the operations of the dispensing device, a dispensing unit to deliver therapeutic fluid into a body of a patient and a sensor to monitor glucose levels in the body of the patient.

12. The method of claim 1, wherein obtaining data comprises determining one or more transmission related values based on one or more of: data transmitted from an external data source and measured data.

13. The method of claim 12, wherein determining one or more transmission related values comprises:
    computing at least one of one or more transmission related values using mathematical relations relating the at least one of the one or more values to at least one of the one or more of: the data transmitted from the external data source and the measured data.

14. The method of claim 12, wherein the one or more transmission related values comprise one or more of:
    availability of transmission frequencies, frequency hopping schedules, pairing status of at least some of the units of the medical device, radio-frequency interference (RFI) level in an area in which the units of the medical device are located, signal-to-noise ratio (SNR) of a first one or more previous transmissions communicated by the units of the medical device and Received Signal Strength Indication (RSSI) data of a second one or more previous transmissions.

15. The method of claim 1, further comprising notifying a user regarding at least one of: the data relating to wireless transmissions and the one or more attributes of the wireless transmissions.

16. The method of claim 1, wherein the medical device comprises one or more of: a therapeutic fluid dispensing device and an analyte sensing device.

* * * * *